US010251667B2

(12) United States Patent
Cohen et al.

(10) Patent No.: US 10,251,667 B2
(45) Date of Patent: Apr. 9, 2019

(54) EXPANDABLE ATHERECTOMY DEVICE

(71) Applicant: Taryag Medical Ltd., Caesarea (IL)

(72) Inventors: Aharon Cohen, Ramat Hashavim (IL); Swi Barak, Caesarea (IL)

(73) Assignee: Taryag Medical Ltd, Caesarea (IL)

( * ) Notice: Subject to any disclaimer, the term of this patent is extended or adjusted under 35 U.S.C. 154(b) by 664 days.

(21) Appl. No.: 14/791,240

(22) Filed: Jul. 2, 2015

(65) Prior Publication Data
US 2015/0335348 A1 Nov. 26, 2015

Related U.S. Application Data

(63) Continuation-in-part of application No. PCT/IL2014/050008, filed on Jan. 5, 2014.
(Continued)

(51) Int. Cl.
*A61B 17/3207* (2006.01)
*A61B 17/32* (2006.01)

(52) U.S. Cl.
CPC ........ *A61B 17/320725* (2013.01); *A61B 17/320758* (2013.01); *A61B 2017/320004* (2013.01);
(Continued)

(58) Field of Classification Search
CPC ........ A61B 17/3207; A61B 17/320725; A61B 17/320758; A61B 2017/320733;
(Continued)

(56) References Cited

U.S. PATENT DOCUMENTS 3,614,953 A 10/1971 Moss et al.
4,936,845 A * 6/1990 Stevens .......... A61B 17/320758
604/22
(Continued)

FOREIGN PATENT DOCUMENTS

CN 102056555 A 5/2011
CN 102056556 A 5/2011
(Continued)

OTHER PUBLICATIONS

Chinese First Office Action, Chinese Application No. 201480006915.1, dated Oct. 8, 2016, 21 pages.
(Continued)

*Primary Examiner* — Diane Yabut
*Assistant Examiner* — Majid Jamialahmadi
(74) *Attorney, Agent, or Firm* — Fenwick & West LLP

(57) ABSTRACT

A device and method for removing atheroma. An expandable atherectomy device comprises a rotatably motor-driven flexible hollow shaft that is slidable over a guidewire introducible through a flexible catheter tube and is coaxial with the longitudinal axis of the guidewire, an expandable cutting unit connected to a distal end of the hollow shaft, and an actuator which is operable to induce selective expansion of the cutting unit. The cutting unit, when expanded, is eccentrically rotatable about the longitudinal axis to cut and remove atheromous material from a blood vessel. In one embodiment, the method also includes the step of drilling an occlusion present in the lumen of a blood vessel by a drill unit connected to the cutting unit.

20 Claims, 23 Drawing Sheets

Related U.S. Application Data

(60) Provisional application No. 61/749,411, filed on Jan. 7, 2013, provisional application No. 61/814,832, filed on Apr. 23, 2013.

(52) U.S. Cl.
CPC ............ *A61B 2017/320766* (2013.01); *A61B 2217/005* (2013.01)

(58) Field of Classification Search
CPC ........... A61B 2017/320766; A61B 17/320708; A61B 2017/320741
USPC ........................................................ 606/159
See application file for complete search history.

(56) References Cited

U.S. PATENT DOCUMENTS

| | | | |
|---|---|---|---|
| 5,030,201 A | | 7/1991 | Palestrant |
| 5,490,859 A | * | 2/1996 | Mische .......... A61B 17/320725 606/159 |
| 5,554,163 A | | 9/1996 | Shturman |
| 6,146,396 A | | 11/2000 | Konya et al. |
| 6,156,046 A | | 12/2000 | Passafaro et al. |
| 6,156,049 A | * | 12/2000 | Lovato ................... A61B 1/015 604/22 |
| 6,494,890 B1 | | 12/2002 | Shturman et al. |
| 6,818,002 B2 | | 11/2004 | Shiber |
| 7,108,704 B2 | | 9/2006 | Trerotola |
| 7,316,697 B2 | | 1/2008 | Shiber |
| 2002/0010487 A1 | | 1/2002 | Evans et al. |
| 2003/0158518 A1 | * | 8/2003 | Schonholz ....... A61B 17/12109 604/104 |
| 2003/0187468 A1 | | 10/2003 | Shiber |
| 2004/0219028 A1 | * | 11/2004 | Demarais ....... A61B 17/320725 417/53 |
| 2007/0088230 A1 | * | 4/2007 | Terashi .............. A61B 17/3207 600/585 |
| 2008/0046000 A1 | * | 2/2008 | Lee ........................ A61B 17/29 606/205 |
| 2008/0228258 A1 | * | 9/2008 | Gerdts ..................... A61F 2/95 623/1.11 |
| 2009/0204135 A1 | * | 8/2009 | Cote .................. A61B 17/3211 606/167 |
| 2009/0270896 A1 | * | 10/2009 | Sullivan ........... A61B 17/32002 606/170 |
| 2010/0121361 A1 | | 5/2010 | Plowe et al. |
| 2011/0087257 A1 | | 4/2011 | To et al. |
| 2013/0103046 A1 | | 4/2013 | Shiber |

FOREIGN PATENT DOCUMENTS

| | | |
|---|---|---|
| CN | 102088920 A | 6/2011 |
| CN | 102573670 A | 7/2012 |
| CN | 102781354 A | 11/2012 |
| CN | 102802544 A | 11/2012 |
| JP | H04-507211 A | 12/1992 |
| JP | H08-509390 A | 10/1996 |
| JP | H08-509639 A | 10/1996 |
| JP | 2001-079031 A | 3/2001 |
| JP | 2001-522631 A | 11/2001 |
| WO | WO 94/08519 A1 | 4/1994 |
| WO | WO 99/29240 A1 | 6/1999 |
| WO | WO 99/44506 A1 | 9/1999 |
| WO | WO 2008/136005 A2 | 11/2008 |
| WO | WO 2009/065078 A1 | 5/2009 |
| WO | WO 2011/081956 A1 | 7/2011 |

OTHER PUBLICATIONS

European Extended Search Report, European Application No. 14735305.6, dated Jul. 28, 2016, 9 pages.
PCT International Search Report, PCT Application No. PCT/IL2014/050008, dated Apr. 13, 2014, 6 pages.
PCT Written Opinion, PCT Application No. PCT/IL2014/050008, dated Apr. 13, 2014, 7 pages.

\* cited by examiner

EXPANDABLE ATHERECTOMY DEVICE

FIELD OF THE INVENTION

The present invention relates to the field of rotational atherectomy devices for removing plaque and clots that have accumulated on a blood vessel wall. More particularly, the invention relates to an expandable atherectomy device.

BACKGROUND OF THE INVENTION

Several methods are currently available to form a channel through a blocked blood vessel. Initially, a guidewire is used to probe a channel through the blockage in the blood vessel in order to reach a downstream unblocked blood vessel portion. After the guidewire has been advanced through the blockage, an angioplasty balloon catheter is passed over the guidewire and is inflated to dilate the blockage.

This method is known to succeed in soft or partial blockages of a blood vessel, through which the guidewire can be easily passed. It carries the risk, however, of causing tears in the arterial wall due to the diameter of the inflated balloon. Moreover, such methods do not remove the atheromatous material from the vessel.

Other methods use catheter devices having a rotating or vibrating tip operated by an external drive unit or power source, which is coupled to the tip by a flexible drive element, such as a cable, spring or shaft. Such devices such as disclosed in U.S. Pat. No. 6,818,002 are introduced into a blood vessel over a guidewire, and the atheroma or blood clot material is shaved from the wall of the artery and may then be aspirated by the catheter out of the vessel in order to prevent distal embolization.

These methods are known to be insufficient to remove all the atheroma or blood clot material from the blood vessel because of the limited size of the rotating tip. For example, the diameter of the rotating tip cannot generally be much larger than the diameter of the catheter, which is usually limited to 1.5-2.5 millimeters. Such devices can form a channel only of this diameter, regardless of the vessel diameter and the atheroma or blood clot material volume.

Some rotating catheters having expandable tips in form of baskets or loops that adapt to the vessel size are known in the prior art, for example US 2002/0010487, U.S. Pat. No. 7,108,704 and US 2013/0103046. The manufacturing costs and the complexity of such catheters are high and their shaft diameter is usually relatively large. Moreover, the design of such devices usually provides poor aspiration capabilities, poor flexibility which limits maneuverability within curved blood vessels, and the inability to open a total occlusion in a blood vessel whose hardness prevents the guidewire from passing therethrough.

Such prior art devices are introduced into the blood vessel through an introducer sheath of a guiding catheter, necessitating that the effective cross section of the shaft used for aspiration will be smaller than the cross section of the introducer sheath or of the guiding catheter.

Expandable devices are also disclosed in U.S. Pat. No. 5,030,201 and U.S. Pat. No. 6,146,396.

U.S. Pat. No. 7,316,697 discloses a vessel cleaning system for removing an obstruction from within a patient's vessel. A flexible distal-agitator is connected to the agitator-shaft and shaped so that it is asymmetrically offset to only one side of the longitudinal axis of the agitator-shaft. The agitator-shaft is extended from an open distal end of the flexible-tube to break the obstruction into pieces while rotating with an effective diameter that is larger than its cross-sectional diameter. The agitator-shaft has difficulty in being introduced to both large and small sized blood vessels. This device cannot be advanced over a guidewire and cannot open a total occlusion.

It is an object of the present invention to provide an atherectomy device that can be selectively introduced to both large and small sized blood vessels.

It is an additional object of the present invention to provide an atherectomy device that can open a total occlusion and to then permit passage of a guidewire downstream to the opened occlusion site, for additional atheroma removal.

Other objects and advantages of the invention will become apparent as the description proceeds.

SUMMARY OF THE INVENTION

The present invention provides an expandable atherectomy device, comprising a rotatably motor-driven flexible hollow shaft that is slidable over a guidewire introducible through a flexible catheter tube and is coaxial with the longitudinal axis of said guidewire, an expandable cutting unit connected to a distal end of said hollow shaft, and an actuator which is operable to induce selective expansion of said cutting unit, wherein said cutting unit, when expanded, is eccentrically rotatable about said longitudinal axis to cut and remove atheromous material from a blood vessel.

In one aspect, the cutting unit is expandable in response to an actuated action which causes two separated ends of the cutting unit to be brought closer together.

In one aspect, the actuator is a longitudinally displaceable adjusting member, to a distal face of which is connected a seal which is sealingly engaged with the housing body and with the inner tube portion, proximal displacement of said adjusting member causing the inner tubular portion to be displaced in a similar direction, whereby to set the cutting unit to a bowed configuration.

In one aspect, the outer tubular portion is formed with a window having a proximal and distal edge, one of said proximal edge and distal edge being contactable by a pin attached to the inner tubular portion at a corresponding extreme position of the adjusting member, whereby to limit the longitudinal displacement of the adjusting member.

In one aspect, the device further comprises an elastic skirt securable to the cutting unit ends for ensuring non-traumatic contact with the blood vessel walls.

In one aspect, the hollow shaft comprises inner and outer tubular portions that are simultaneously rotatable while one of said inner and outer tubular portions slides over the other in a direction substantially parallel to the longitudinal axis.

In one aspect, the device further comprises a housing body in which a motor for rotatably driving the hollow shaft is housed, and connection means for connecting the catheter tube to a distal tip of said housing body.

In one aspect, the device further comprises an aspiration system for removal of the disintegrated atheroma particles which is in communication with the interior of the catheter tube. The aspiration system may comprise a vacuum pump, a first aspiration line extending from an annular space between the housing body distal tip and the outer tubular portion to said vacuum pump, a collection bag to which are drawn the disintegrated atheroma particles, and a second aspiration line extending from said vacuum pump to said collection bag.

In one aspect, the motor is also drivingly engaged with an element configured to generate a vacuum for inducing aspiration of disintegrated atheroma particles.

In one aspect, the cutting unit is formed integrally with the outer tubular portion.

In one aspect, the cutting unit is made of a shape-memory alloy which, when heated, will change its shape and be set to the bowed configuration.

In one aspect, the outer tubular portion is connected to the outer tubular portion by discontinuously applied laser welding.

The present invention is also directed to a method for removing atheroma, comprising the steps of providing an atherectomy device with a a rotatably motor-driven flexible hollow shaft that is slidable over a guidewire introducible through a flexible catheter tube and is coaxial with the longitudinal axis of said guidewire, and with a cutting unit that is connected to a distal end of said hollow shaft, actuating said cutting unit to initiate expansion of said cutting unit, and cutting and removing atheromatous material from blood vessel walls during asymmetric rotation of said cutting unit about said longitudinal axis relative to said hollow shaft.

In one aspect, the cutting unit is selectively and gradually actuated until its diameter approximates the diameter of the blood vessel at the site of the atheroma, to maximize atheromatous material removal.

In one aspect, the atherectomy device is advanced over a guidewire inserted within the blood vessel while the cutting unit is in a collapsed condition until a distal end of the device protrudes from a catheter tube and is adjacent to the atheroma.

In one aspect, the removed material is aspirated through the lumen of the catheter tube upon activation of an aspiration system.

In one aspect, the catheter tube is replaced in order to access a different sized blood vessel.

In one aspect, the method further comprises the step of drilling an occlusion present in the lumen of a blood vessel by a drill unit connected to the cutting unit.

DETAILED DESCRIPTION OF PREFERRED EMBODIMENTS

The atherectomy device of the present invention comprises a tube embodied by a motor-driven coaxial flexible hollow shaft that is slidable over a guidewire. The coaxial flexible hollow shaft includes inner and outer tube layers that rotate simultaneously while sliding one over the other in a direction parallel to the longitudinal axis of the shaft.

Two ends of a flexible cutting unit for removing the atheroma or blood clot from the interior of the blood vessel are connected to the distal end of the inner and outer layers, respectively. An adjusting member is provided for selectively expanding the flexible cutting unit away from the longitudinal axis of the shaft, typically by controlled retraction of the inner layer by sliding movement inside the outer layer. Retraction of the inner layer brings the ends of the flexible cutting unit together, thus causing the strip to bow outwardly away from the longitudinal axis of the shaft and enlarging the area encompassed by the flexible cutting unit. The expanded cutting unit facilitates disintegration and removal of the atheroma from the blood vessel when rotating. A skirt securable to the cutting unit ends ensures non-traumatic contact with the blood vessel walls.

Figure 30:
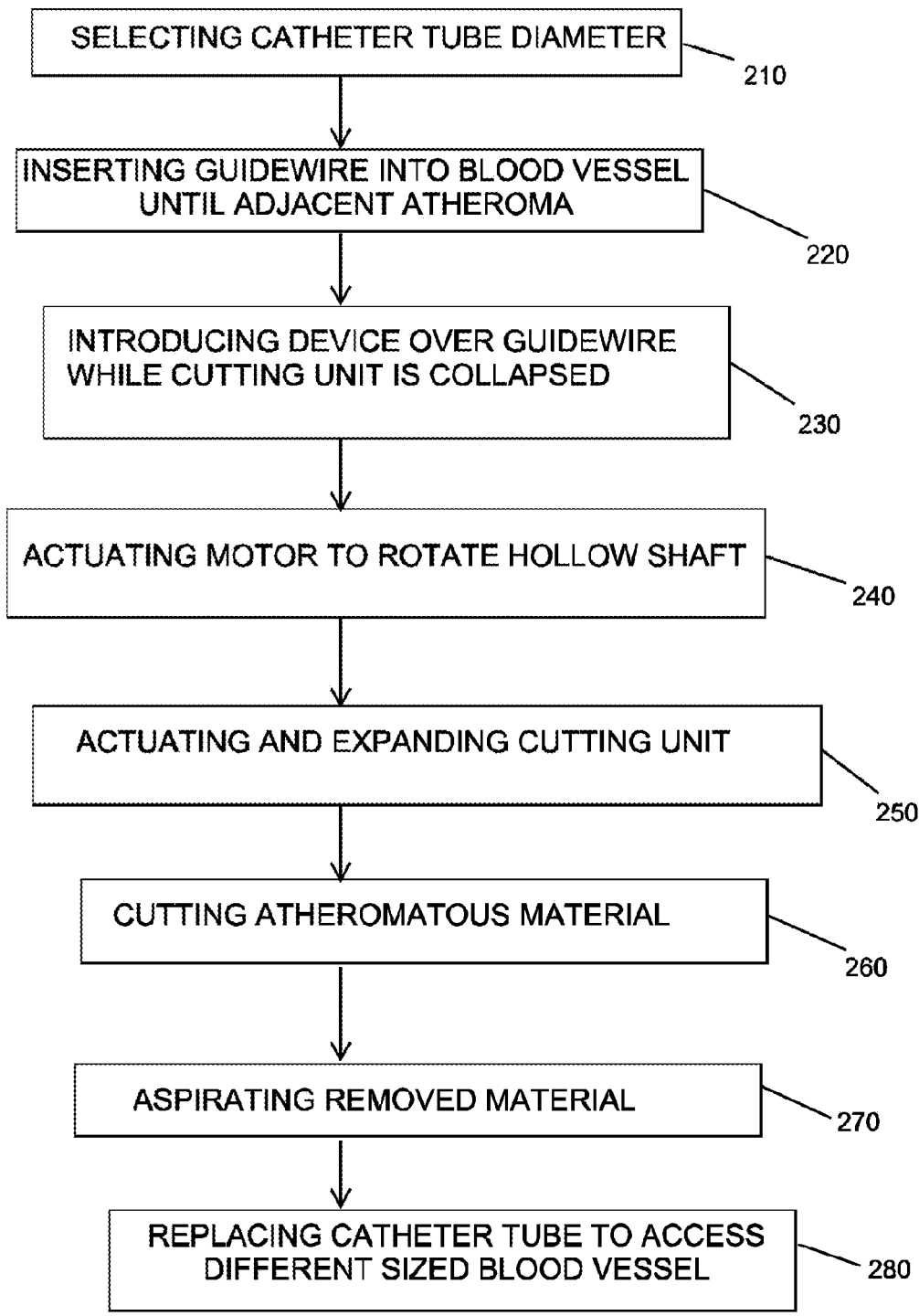
FIG. 30 is a method for removing atheroma, according to one embodiment of the invention.

Broadly speaking, atheroma may be removed by manipulating the device of the present invention according to the method set forth in FIG. 30. Firstly, the physician selects in step 210 the diameter of a catheter tube within which the hollow shaft is disposed, in accordance with the diameter of a given blood vessel. The guidewire is then inserted into the blood vessel in step 220 until its distal end is adjacent to the site of the atheromatous material. The atherectomy device is then advanced over the guidewire in step 230 while the cutting unit is in the collapsed condition, until the distal end of the device protrudes from a catheter tube and is adjacent to the atheroma. After the motor is activated in step 240, the hollow shaft is rotated. While the hollow shaft is rotating, the cutting unit is caused to expand in step 250 by means of a suitable actuator to asymmetrically cut and remove the atheromatous material from the walls of the blood vessel in step 260. The cutting unit may be selectively and gradually actuated until its diameter approximates the diameter of the blood vessel at the site of the atheroma, to maximize atheromatous material removal. The removed material is aspirated through the lumen of the catheter tube upon activation of an aspiration system in step 270.

When it is desired to perform an atheroma removal operation within a narrow blood vessel, the catheter tube is easily replaced in step 280 while the diameter of the hollow shaft remains the same, allowing an operator to choose between accessibility into a narrow blood vessel or improved aspiration capabilities through a large diameter catheter tube.

Figure 1:
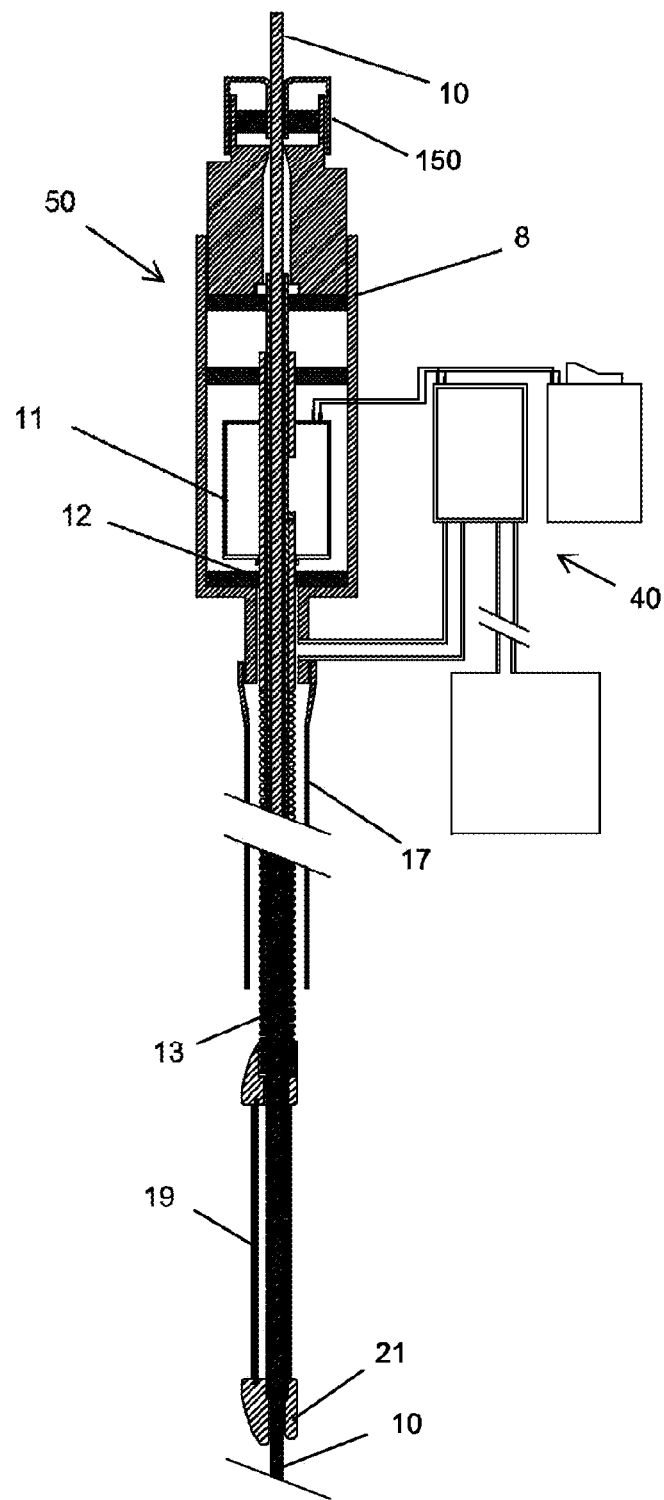
FIG. 1 is a partial longitudinal cross section of an atherectomy device shown in a collapsed condition, according to one embodiment of the present invention.

FIG. 1 illustrates a partial longitudinal cross section of an expandable atherectomy device, generally indicated by numeral 50, according to one embodiment of the present invention. The flexible cutting unit 19 is shown in a collapsed condition.

Atherectomy device 50 comprises a flexible rotatable hollow shaft 13, which is received within the interior of an elongated and percutaneously introducible, flexible catheter tube 17, e.g. made of plastic. Hollow shaft 13 comprises a proximal relatively rigid portion consisting of outer tubular portion 14 and inner tubular portion 16, and a distal relatively flexible portion consisting of outer tubular portion 14A and inner tubular portion 16A (see FIG. 4). Guidewire 10 in turn is received within the interior of hollow shaft 13 by means of introduction unit 150. The proximal end of catheter tube 17 is connected to a distal portion of catheter body 8, within which is housed a motor 11 for driving hollow shaft 13. Two longitudinally spaced cutting unit holders 20 and 21 are carried by hollow shaft 13, at a distal end thereof. An aspiration system 40 for removal of the disintegrated atheroma particles is in communication with the interior of catheter tube 17.

Figure 2:
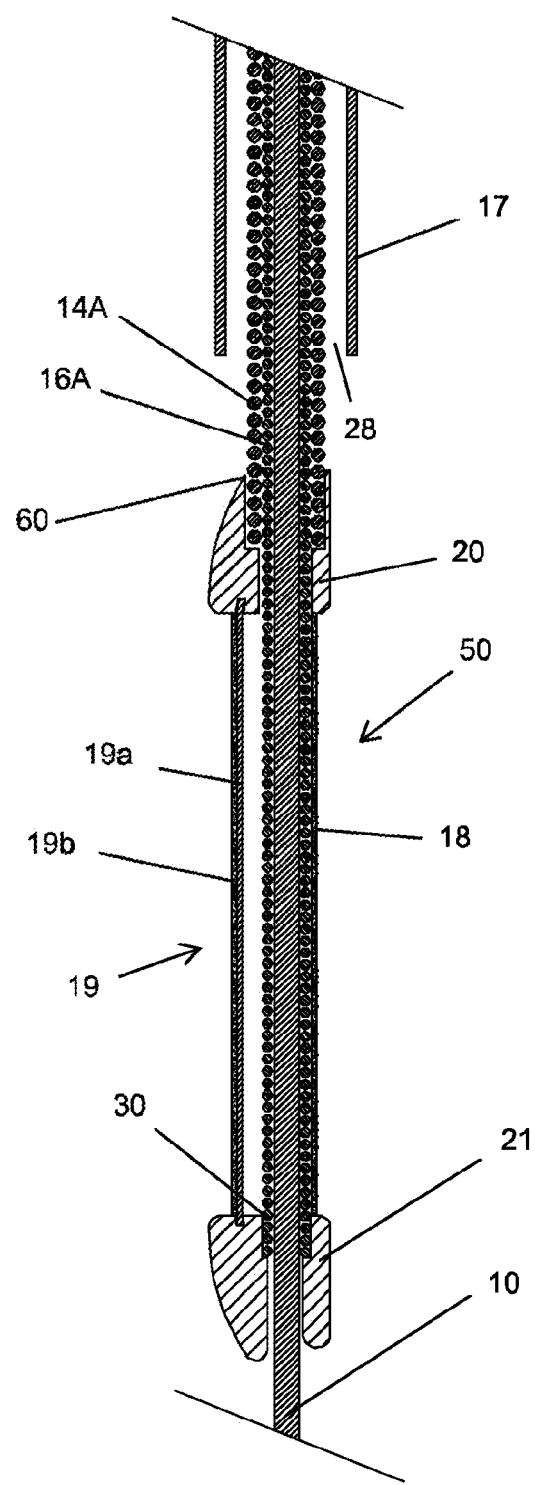
FIG. 2 is an enlargement of FIG. 1, showing a distal portion of the atherectomy device of FIG. 1 including a cutting unit.

FIG. 2 is an enlargement of FIG. 1, showing a distal portion of atherectomy device 50, which is introducible within a blood vessel. The relatively flexible portion of the coaxial flexible hollow shaft comprises a closely-wound spiral outer tubular layer 14A and an inner tubular layer 16A, received within the interior of flexible catheter tube 17. Alternatively, one or both of the inner tube and outer tube may be made of one or more wires or strips formed together.

Spiral components that can be suitable for the present invention can be made of stainless steel or Nitinol and include the ACTON series of cable tube type FLAT or STD made by Asahi Intecc (Asahi Intecc Co. Ltd., Japan), or the HSS® series of tubes made by Fort Wayne Metals (Fort Wayne, Ind.). The one or more wires or strips that are formed together to define this closely-wound spiral or tube may all have the same diameter, or alternatively, some wires or strips may have a larger diameter than others, thereby forming a coaxial flexible hollow shaft with round or elliptical outer contour and a closely rounded internal lumen. The spiral components may assume a screw shape to assist in conveying the disintegrated material.

Nitinol, or any other selected material for use during an atheroma removal operation, may be applied only at or near the distal end of the hollow shaft, for increased savings.

A distal portion of the outer tubular layer 14A may be welded to the proximal cutting unit holder 20 at a proximal and radially inward seat 60 thereof. The inner tubular layer 16A is longer than the outer tubular layer and may be welded to the distal cutting unit holder 21 at weld point 30 along its proximal, substantially planar edge thereof. The guidewire 10 extends through the interior of cutting unit holders 20 and 21 while contacting the inner tube 16A.

Figure 3:
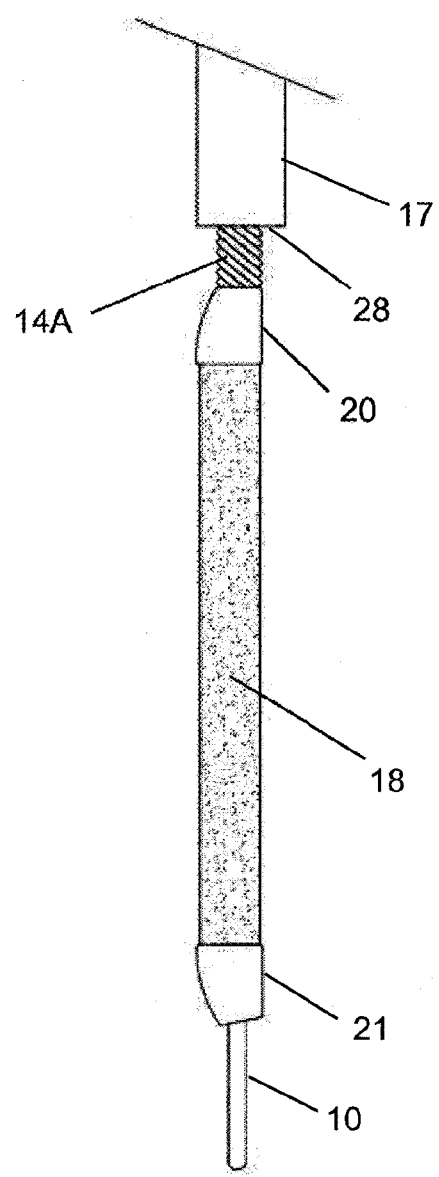
FIG. 3 is a longitudinal view of the distal portion of the atherectomy device of FIG. 1, showing an elastic skirt that covers and surrounds the cutting unit of FIG. 2.

The flexible cutting unit 19 for removing the atheroma extends between cutting unit holders 20 and 21, generally parallel to the longitudinal axis of the shaft, and is shown to consist of two strip portions 19a and 19b, although it may be comprised of a single strip portion. The flexible cutting unit may be made of any type of any suitable flexible material, such as plastic, elastic material, metal and shape memory metal, including the material from which outer tubular layer 14A and inner tubular layer 16A are made. A slack elastic skirt 18 that covers and surrounds the flexible cutting unit between cutting unit holders 20 and 21 has a sleeve shape, and is shown in its entirety in FIG. 3.

Disintegrated atheroma particles are removable by the aspiration system through the gap 28 formed between outer tubular layer 14A of the coaxial shaft and catheter tube 17.

Figure 4:
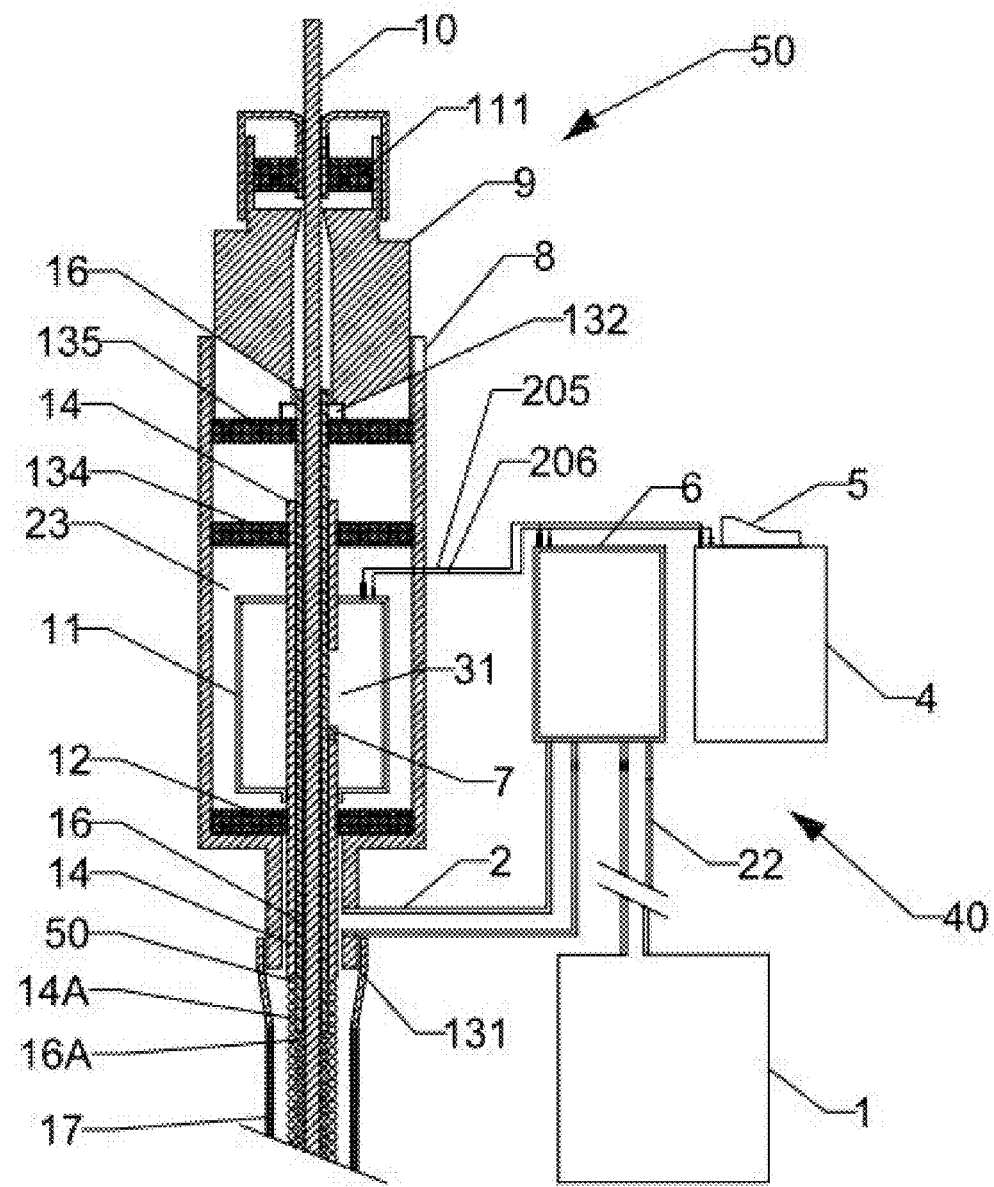
FIG. 4 is an enlargement of FIG. 1, showing a proximal portion of the atherectomy device including an aspiration system.

FIG. 4 is an enlargement of FIG. 1, showing a proximal portion of atherectomy device 50, which is generally disposed externally to a patient's body.

Catheter tube 17 is connected to the distal tip of catheter body 8 by schematically illustrated connection means 131, which may be a flexible shaft connector, a regular Luer lock type connector, or any other suitable connector. Connection means 131 may be detachable, to allow catheter tube 17 to be replaced by one of a different diameter, depending on the size of the given blood vessel to be treated.

The aspiration system 40 comprises a miniature vacuum pump 6 and a collection bag 1, to which are drawn the disintegrated atheroma particles via first aspiration line 2 extending from the annular space between the distal narrowed tip of catheter body 8 and outer tubular portion 14 to vacuum pump 6, and second aspiration line 22 extending from vacuum pump 6 to collection bag 1. Battery unit 4 having a switch 5 powers both vacuum pump 6 and motor 11. The aspiration system may also assume the configuration shown in FIG. 22.

Motor 11 connected to battery unit 4 by wires 205 and 206 is housed within chamber 23 of catheter body 8 between distal seal 12 and intermediate seal 134, which are fixed and through which tubular portions 14 and 16 of the hollow coaxial shaft pass. Motor 11, which is sealed by fixed seals 12 and 134 and by displaceable seal 135, is drivingly engaged with outer tubular portion 14.

Alternatively, the same motor may be used for both for rotating the hollow shaft and for generating a vacuum that induces aspiration of the atheroma particles. A crank fixed on the motor shaft converts rotary movement into linear movement, so that a flexible diaphragm will be moved up and down, to vary the volume of a pump chamber in fluid communication with the interior of the catheter tube, by means of a connecting rod and an eccentric on the motor shaft. During a downstroke, air is drawn into the enlarged pump chamber. Air is then expelled during an upstroke when the volume of the pump chamber is reduced. One-way valves may be used to control the direction of air flow.

A longitudinally displaceable adjusting member 9 for initiating selective expansion of the flexible cutting unit, the structure of which will be described hereinafter, is fitted within catheter body 8. A seal 135 connected to the distal face of adjusting member 9 is sealingly engaged with the inner wall of catheter body 8. The proximal end of inner tubular portion 16 is connected by adhesion or laser welding to rotating bearing 132, which is seated in a complementary cavity 141 formed in adjusting member 9 (see FIG. 16) and in contact with the proximal face of seal 135. This arrangement allows inner tubular portion 16 to be longitudinally displaced together with adjusting member 9 in or out of catheter body 8 while simultaneously rotating.

The relatively rigid outer tubular portion 14 is connected by laser welding 50 to the relatively flexible outer tubular portion 14A, and the relatively rigid inner tubular portion 16 is connected by laser welding to the relatively flexible inner tubular portion 16A.

Shrinkage may be prevented by discontinuously applying laser welding, for example at predetermined intervals.

Figure 5:
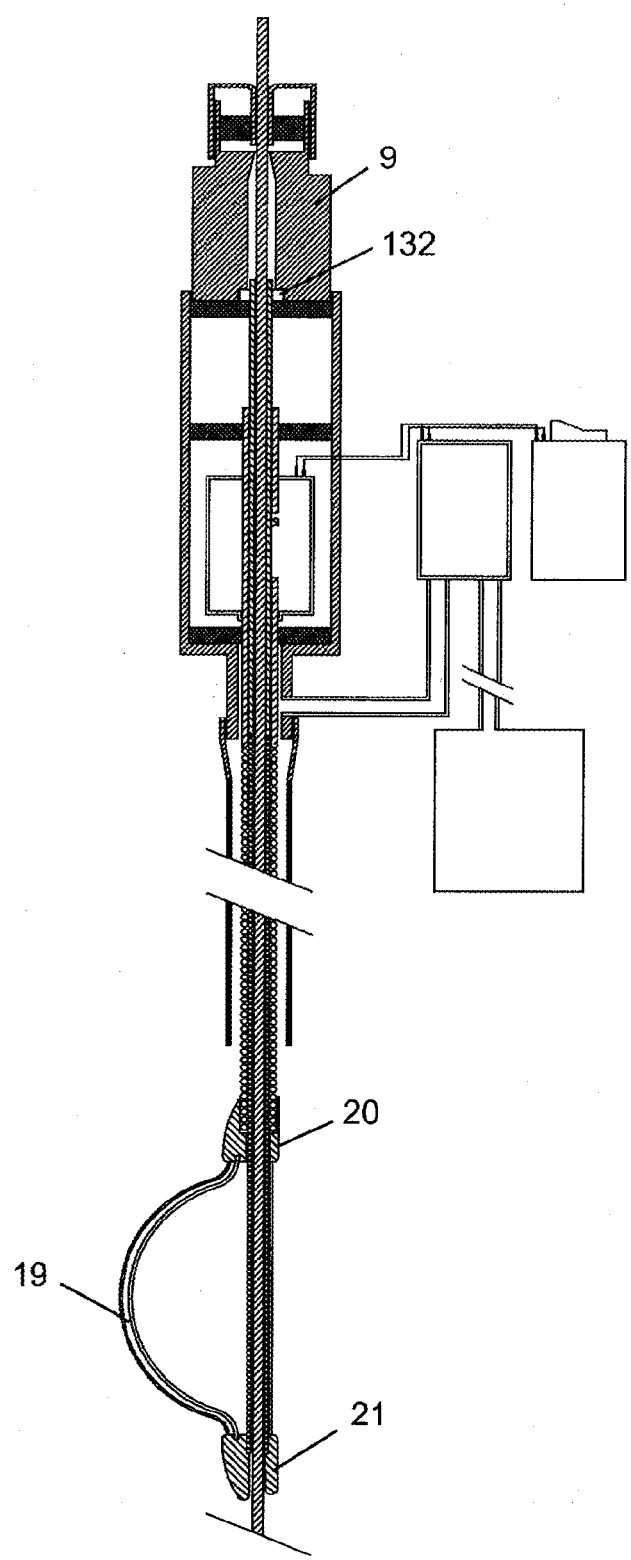
FIG. 5 is a partial longitudinal cross sectional view of the atherectomy device of FIG. 1, shown in an expanded condition.
Figure 6:
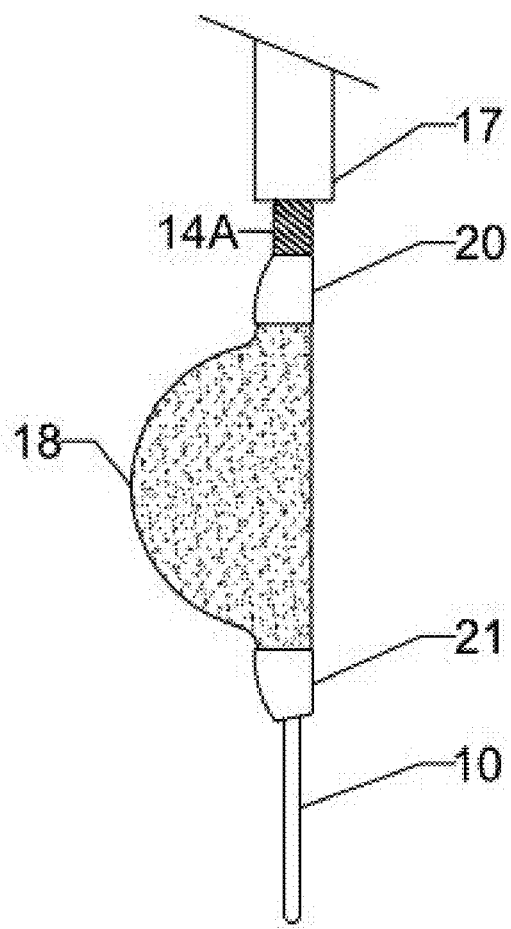
FIG. 6 is a longitudinal view of the distal portion of the atherectomy device of FIG. 5, showing the skirt of FIG. 3 when stretched.

Since the outer tubular layer is not longitudinally displaceable and is connected to proximal cutting unit holder 20, and the inner tubular layer connected to both distal cutting unit holder 21 and rotating bearing 132 is longitudinally displaceable, proximal displacement of adjusting member 9 reduces the spacing between cutting unit holders 20 and 21 and causes the flexible cutting unit 19 to bow outwardly and expand, as shown in FIG. 5, while the elastic skirt 18 surrounding the flexible cutting unit is forced to stretch to a sort of sail or omega shape and become elongated, as shown in FIG. 6. Conversely when adjusting member 9 is distally displaced, cutting unit holders 20 and 21 are caused to be separated by a maximum extent, so that the expanded cutting unit 19 is forced to collapse and straighten so as to be substantially parallel to the longitudinal axis of guidewire 10, as shown in FIG. 1.

Figure 7:
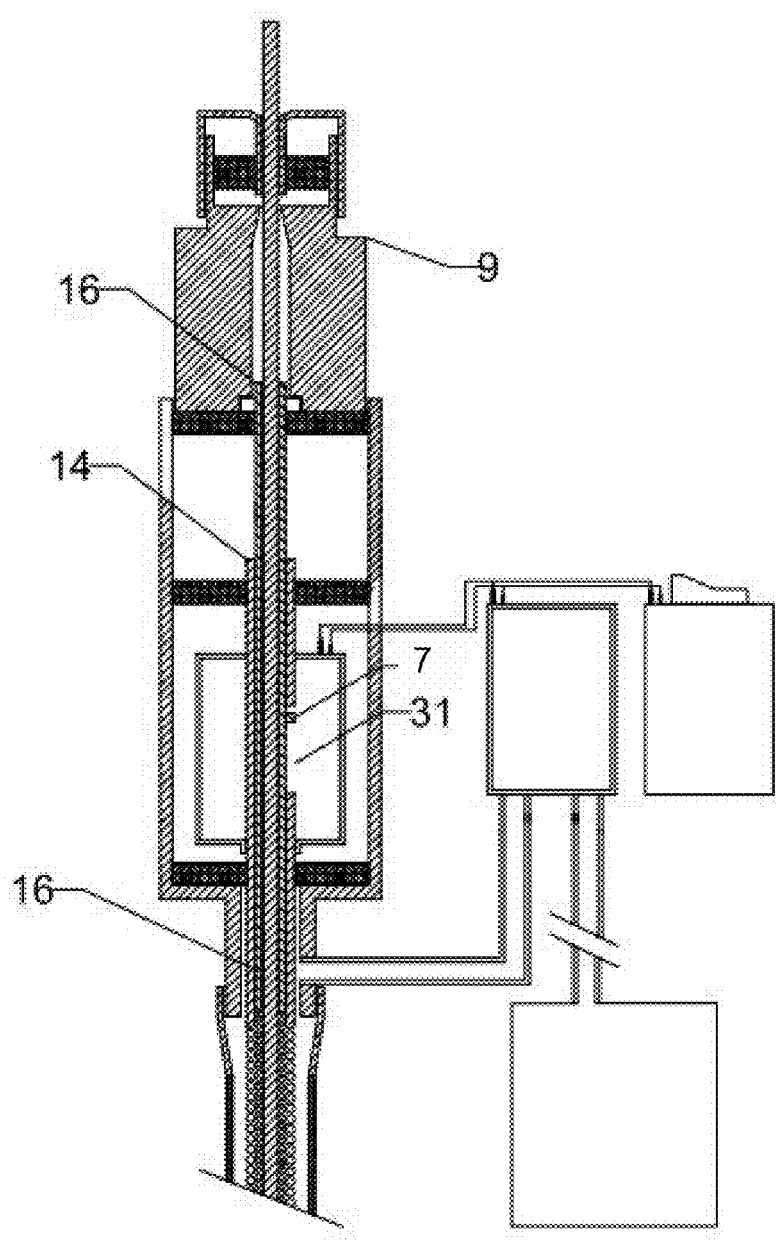
FIG. 7 is an enlargement of FIG. 5, showing a proximal portion of the atherectomy device.

To limit the longitudinal displacement of adjusting member 9, relatively rigid outer tubular portion 14 is formed with a long and narrow window 31 that may be positioned within the confines of motor chamber 23. Within the interior of window 31 a pin 7 welded or otherwise attached to relatively rigid inner tubular portion 16 is allowed to change its position without interference while adjusting member 9 is being longitudinal displaced. However, when pin 7 contacts one of the lower and upper edges of window 31, as shown in FIGS. 4 and 7, respectively, at a corresponding extreme position of adjusting member 9 and of inner tubular portion 16 connected thereto, additional longitudinal displacement is a same direction is prevented. The width of window 31 is slightly more than the width of pin 7, so that when outer tubular portion 14 is rotating and pin 7 is in contact with a window edge, inner tubular portion 16 is caused to rotate as well.

Figure 8:
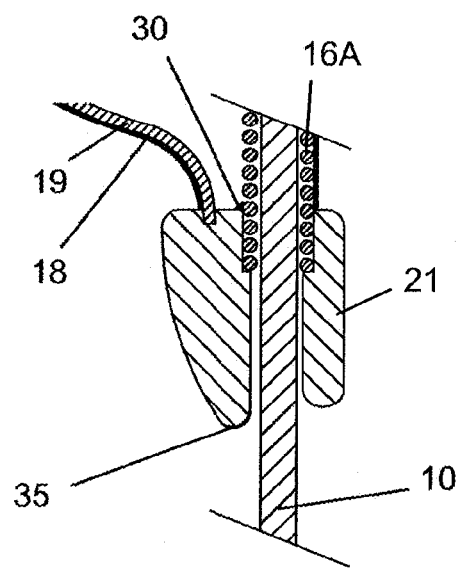
FIG. 8 is a longitudinal cross sectional view of a distal cutting unit holder.

FIG. 8 illustrates the structure of distal cutting unit holder 21. The proximal planar edge of cutting unit holder 21 is welded to inner tubular portion 16A at point 30. The distal end 35 of cutting unit holder 21 may be rough and abrasive in order to improve penetration into hard materials, produced by surface treatment or by an applied layer such as diamond grains. For this embodiment, the flexible cutting unit 19 may be a flexible wire such as Nitinol wire, plastic wire or any other suitable flexible material, and its distal end may be fixed within a bore formed in cutting unit holder 21. This bore is preferably not parallel to the longitudinal axis of guidewire 10, but rather is formed at an angle thereto in order to urge flexible cutting unit 19 to bow outwardly, i.e. away from guidewire 10. This angular bore positioning is also applicable to the proximal end of the flexible cutting unit 19.

Figure 20:
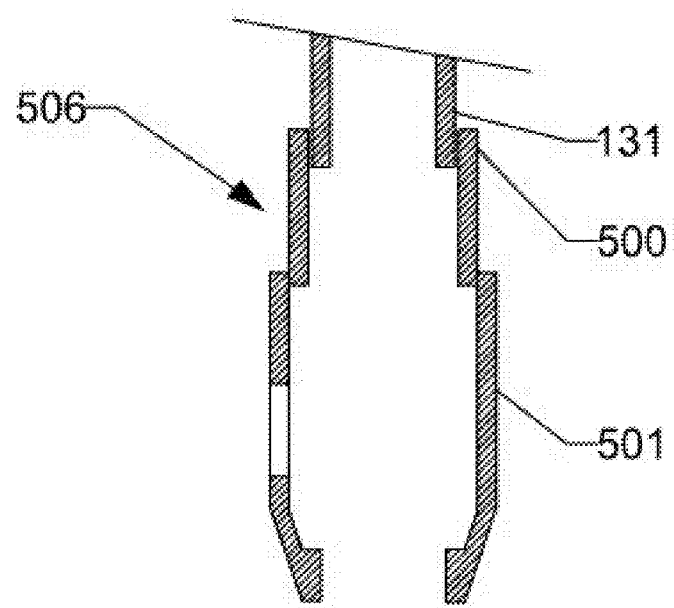
FIG. 20 is a longitudinal cross sectional view of a telescopingly expandable adaptor, shown in an extended condition.
Figure 21:
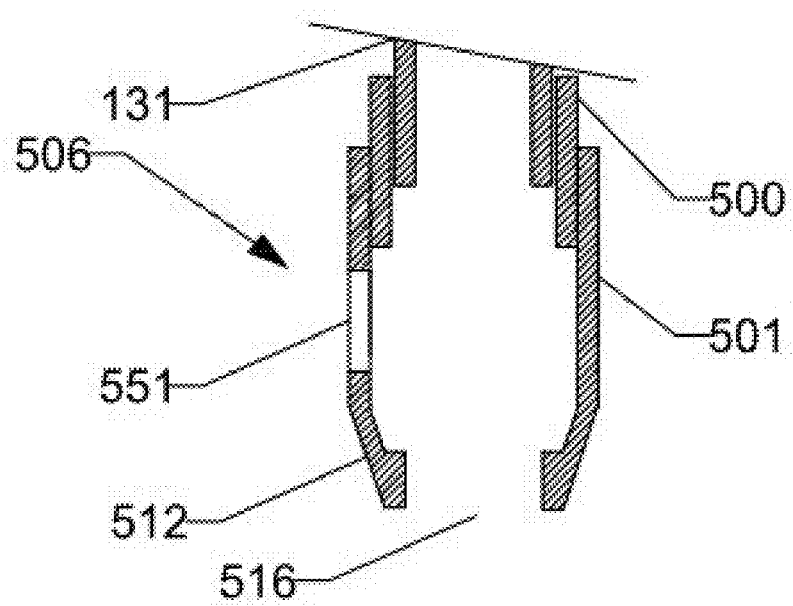
FIG. 21 is a longitudinal cross sectional view of the adaptor of FIG. 20, shown in a retracted condition.
Figure 22:
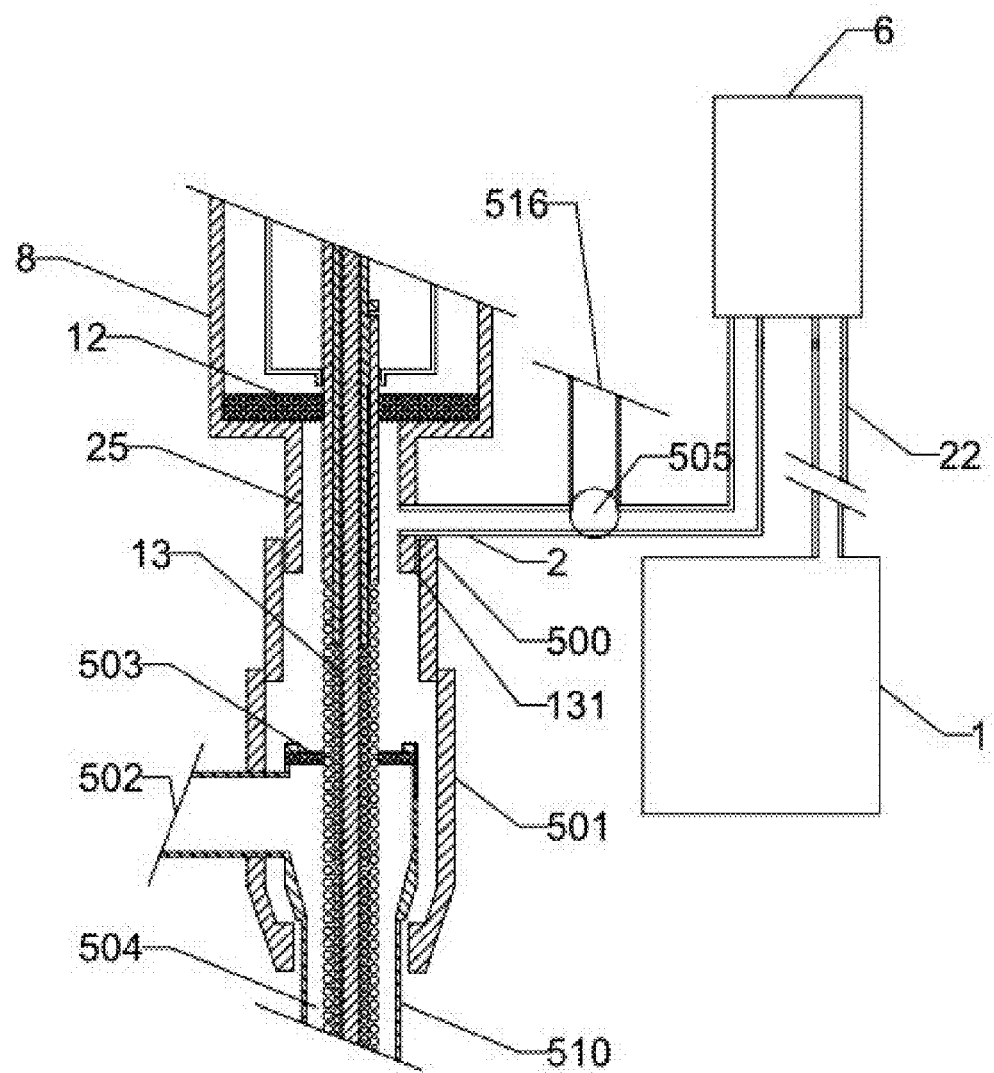
FIG. 22 is a longitudinal cross sectional view of a catheter tube side arm fitted in a section of the adaptor of FIG. 20.

FIGS. 20-22 illustrate an adjustable adaptor for use to compensate for a difference in length between the catheter tube and hollow shaft.

A telescopingly expandable adaptor 506 is shown in an extended condition in FIG. 20 and in a retracted condition in FIG. 21. Adaptor 506 comprises a plurality of sections, e.g. sections 500 and 501, having a gradually increasing width to provide a telescoping capability. The most proximally disposed section 500 is connected by connection means 131, e.g. a Luer connector, to the distal tip 25 of catheter body 8. The sections are in sliding contact with each other when being retracted in order to set adaptor 506 to a desired length. The most distally disposed section 501 is formed with an opening 551 in which catheter tube side arm 502 shown in FIG. 22 can be fitted. Section 501 has a distal angled element 512 defining an opening 516 through which the catheter tube can extend.

In the arrangement shown in FIG. 22, side arm 502 of catheter tube 510 is fitted in the opening of adaptor section 501. This arrangement allows hemostasis valve 503 operatively connected to side arm 502 to be received in the interior of section 501 and catheter tube 510 to extend distally below hemostasis valve 503. Hemostasis valve 503, which may be formed with a central opening in order to accommodate the disposition of hollow shaft 13 extending distally within the lumen 504 of catheter tube 510, may be actuated by an external control device to initiate hemostasis for a portion of the blood vessel to which catheter tube 510 is guided.

By providing first aspiration line 2 with a three-way stopcock valve 505 which is controlled by an actuator, aspiration of disintegrated particles may be directed through side arm 502. For example, vacuum pump 6 may be sufficiently operated when stopcock valve 505 is opened to draw the disintegrated particles through the lumen 504 of catheter tube 510. During aspiration of the disintegrated particles, stopcock valve 505 may be suddenly actuated to occlude first aspiration line 2, whereupon the particles are discharged through side arm 502 to arm portion 516 with which stopcock valve 505 is also operatively connected, and then to vacuum pump 6 and collection bag 1.

Figure 9:
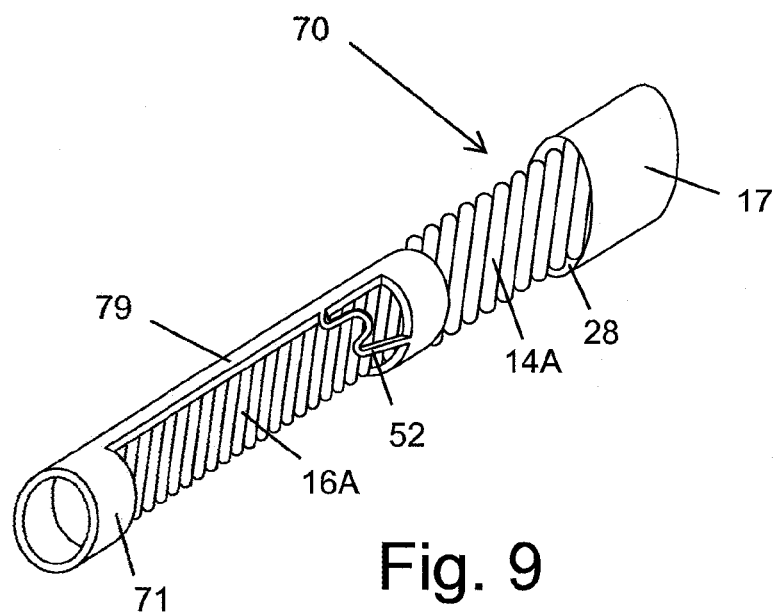
FIG. 9 is a perspective view of the distal end of an atherectomy device according to another embodiment of the invention.

FIG. 9 illustrates the distal end of an atherectomy device 70 according to another embodiment. In this embodiment, the flexible cutting unit 79 is produced by micro-laser cutting of a tube 71. The distal end of tube 71 is connected to the distal end of inner tubular portion 16A, and the proximal end of tube 71 is connected to the distal end of outer tubular portion 14A. Flexible cutting unit 79 may be provided with additional supports cut from a tube 52, in similar fashion to the struts used in stents, to facilitate bowing of flexible cutting unit upon proximal displacement of adjusting member. The aspiration of the removed disintegrated particles is through the annular space 28 between outer tubular portion 14A and catheter tube 17.

Figure 10:
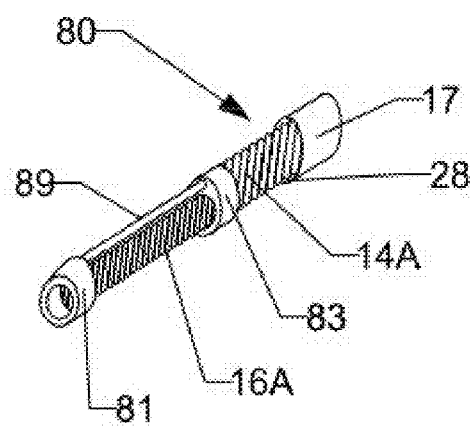
FIG. 10 is a perspective view of the distal end of an atherectomy device according to another embodiment of the invention.

FIG. 10 illustrates the distal end of an atherectomy device 80 according to another embodiment. In this embodiment, the flexible cutting unit 89 is configured by a flexible wire, or by a strip of metal or plastic, which is attached to distal cutting unit holder 81. Distal cutting unit holder 81 is connected to the distal end of inner tubular portion 16A and to proximal cutting unit holder 83, which is connected to the distal end of outer tubular portion 14A. Cutting unit holders 81 and 83 may have an elliptical cross section.

Figure 28:
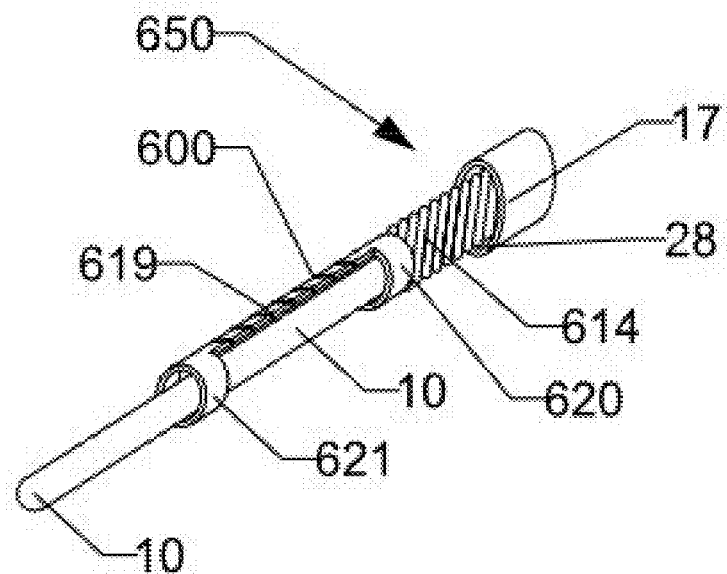
FIG. 28 is a perspective view of the distal end of an atherectomy device according to another embodiment of the invention, shown in a collapsed condition.
Figure 29:
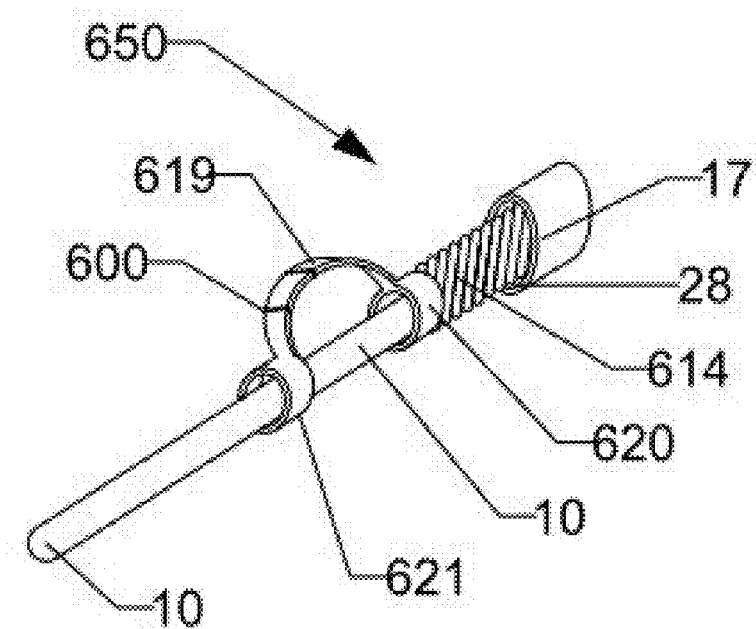
FIG. 29 is a perspective view of the distal end of the atherectomy device of FIG. 28, shown in an expanded condition.

FIGS. 28 and 29 illustrate the distal end of an atherectomy device 650 according to another embodiment. In this embodiment, the cutter unit 619 is made of a shape-memory alloy such as Nitinol which, when heated, will change shape and outwardly bow.

In FIG. 28, cutter unit 619, connected to, or is integral with, holders 620 and 621 through which guidewire 10 passes, is shown to be in a collapsed condition when subjected to the low temperature, or Martensite phase, of approximately less than 37° C. Heating member 600 e.g. nickel-chrome (Ni—Cr) wire or strip, is twisted around cutter unit 619, but may also be attached to one of the sides of the cutter unit. In order to provide electrical isolation and good heat transmission, heating member 600 may be coated with a silicone layer or a polymer layer, e.g. Parylene. The ends of heating member 600 are connected to outer tubular portion 614, which is made of conductive material, e.g. wires made of a stainless steel (Stst) or Nitinol alloy, and in turn is connected to an external electrical power source. Alternatively, additional wires may be connected from the heating member to the power source.

In FIG. 29, cutter unit 619 is shown to be in an expanded condition, after electrical power has been supplied to heating member 600. Heating member 600 is operable to cause cutter unit 619 to be heated at least 2-10° C., so as to be subjected to the high temperature, or the Austenite phase, for inducing a change in shape of cutter unit 619. The local temperature of cutter unit 619, which is sufficiently high to ablate atheroma, will remain substantially constant by supplying a controlled current. Once the flow of current is terminated, cutter unit 619 will cool down to the blood temperature and will return to the Martensite phase and to its original straight shape.

FIGS. 11-15 illustrate another embodiment wherein the cutting unit is formed integrally with the outer tubular portion.

Figure 11:
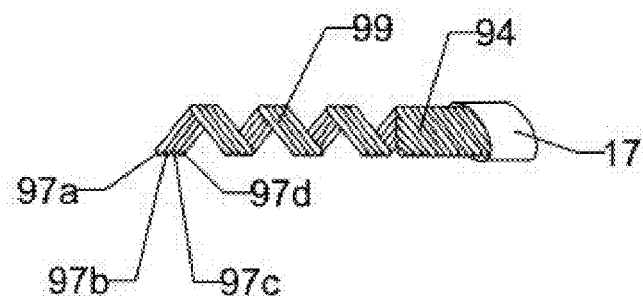
FIG. 11 is a perspective view of the outer tubular portion of a coaxial hollow shaft according to another embodiment of the invention.

As shown in FIG. 11, outer tubular portion 94 of the coaxial hollow shaft, which passes through catheter tube 17, is configured by a plurality of elongated elements 97, e.g. wires or strips, tightly wound about the longitudinal axis such that each elongated element is positioned obliquely with respect to the longitudinal axis. Two or more adjacent elongated elements 97 may be connected together. Alternatively, none of the elongated elements 97 are connected together. The hollow shaft distal end is formed in such a way that four elongated elements 97a-d, or any other suitable number, are longer than the other elongated elements that do not distally extend beyond outer tubular portion 94, so that elements 97a-d can function as the flexible cutting unit 99.

Figure 12:
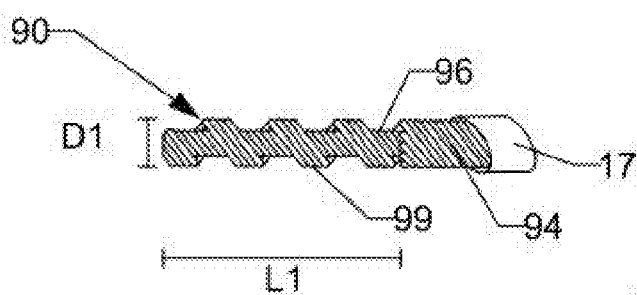
FIG. 12 is a perspective view of the distal end of an assembled atherectomy device employing the outer tubular portion of FIG. 11, shown in a collapsed condition.

FIG. 12 illustrates the distal end of atherectomy device 90 in a collapsed condition. Inner tubular portion 96 of the coaxial hollow shaft is shown to longitudinally extend internally to both outer tubular portion 94 and flexible cutting unit 99. The length of cutting unit 99, i.e. distally of inner tubular portion 96, is L1 and its diameter is D1.

Figure 14:
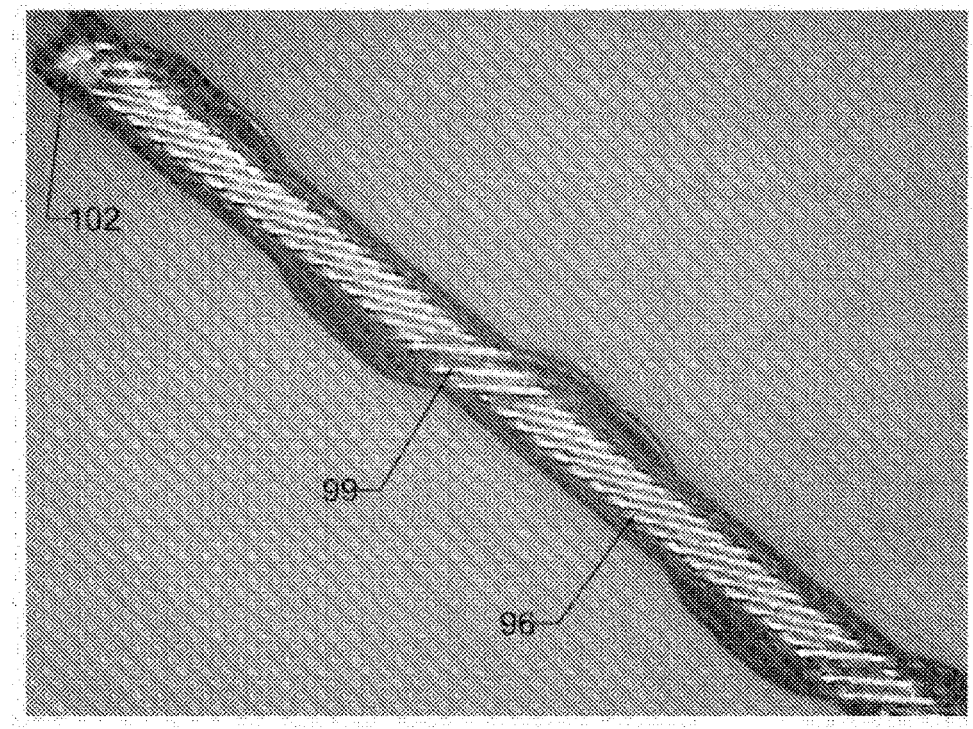
FIG. 14 is a picture of the atherectomy device shown in FIG. 12.

As shown in FIG. 14, the distal ends of cutting unit 99 are connected to the distal end of inner tubular portion 96 at connection point 102, e.g. a welding point.

Figure 13:
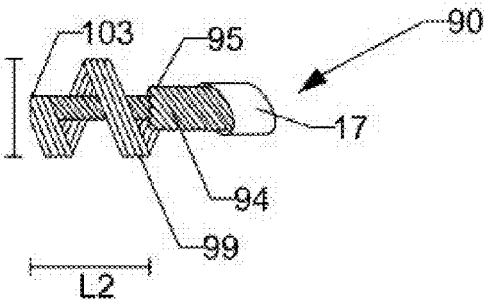
FIG. 13 is a perspective view of the distal end of the atherectomy device of FIG. 12, shown in an expanded condition.
Figure 15:
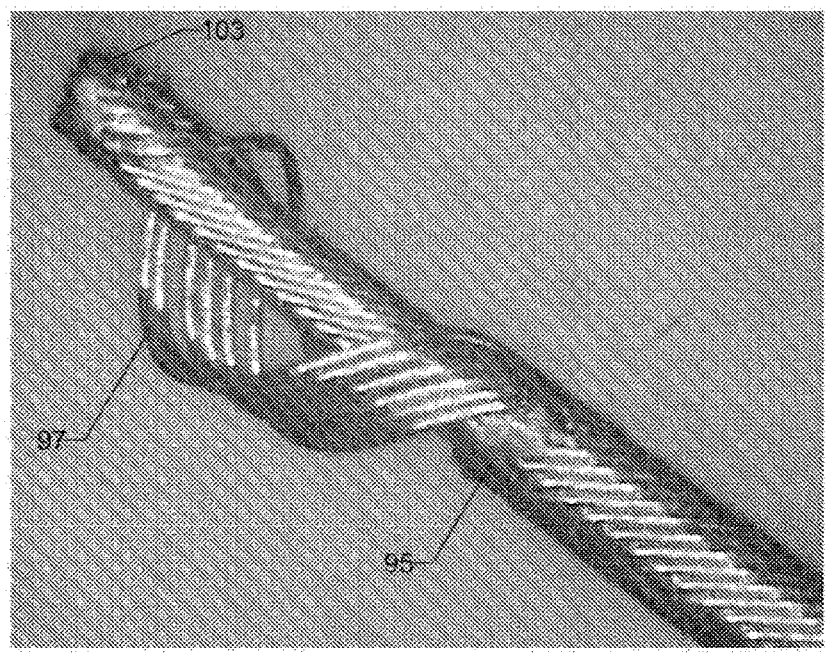
FIG. 15 is a picture of the atherectomy device shown in FIG. 13.

FIGS. 13 and 15 illustrate the distal end of atherectomy device 90 in an expanded condition. In this embodiment, expansion of cutting unit 99 is achieved by proximally displacing the adjusting member, causing the distal end 95 of outer tubular portion 94 and the fixed distal end 103 of cutting unit 99 to be brought together. When the length of cutting unit 99 is reduced to L2, the elongated elements 97 flex to achieve an expanded diameter of D2. An elastic skirt may cover cutting unit 99. The aspiration of disintegrated material may be directed through the annular space between catheter tube 17 and outer tubular portion 94.

In the embodiment of FIGS. 31-35, the distal end of atherectomy device 300 is provided with an atraumatic drill unit 360 and with a stress relief unit 380.

Figure 31:
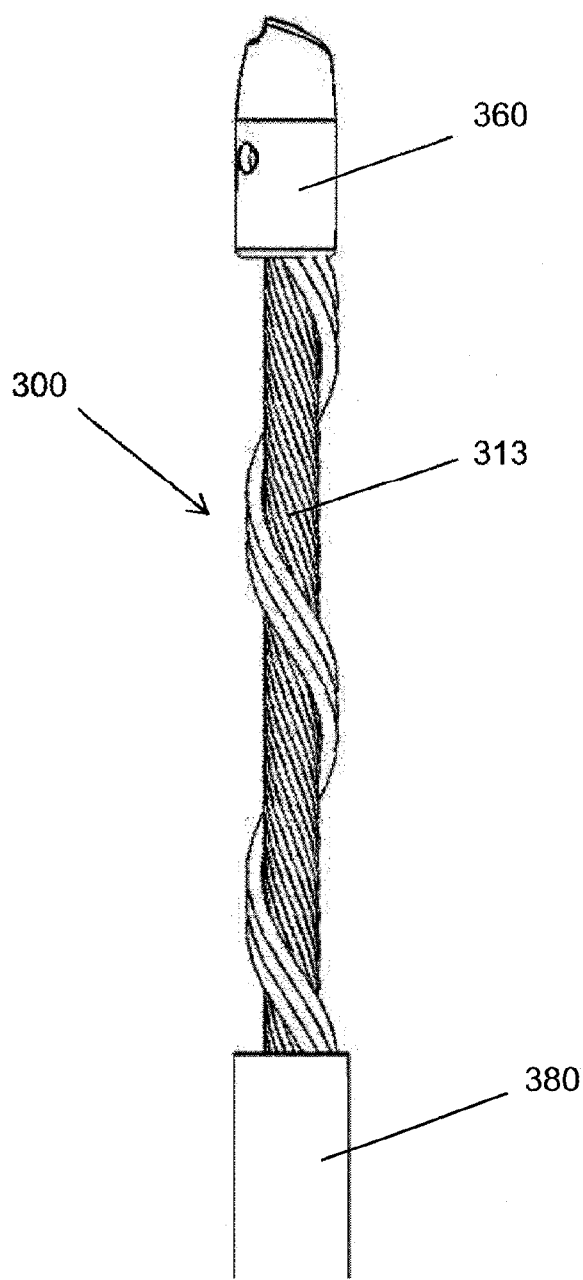
FIG. 31 is a front view of the distal end of an atherectomy device according to another embodiment of the invention, provided with a drill unit and a stress relief unit.

As shown in FIG. 31, stress relief unit 380 is positioned proximally with respect to drill unit 360, and hollow shaft 313 extends between drill unit 360 and stress relief unit 380.

Figures 32, 33:
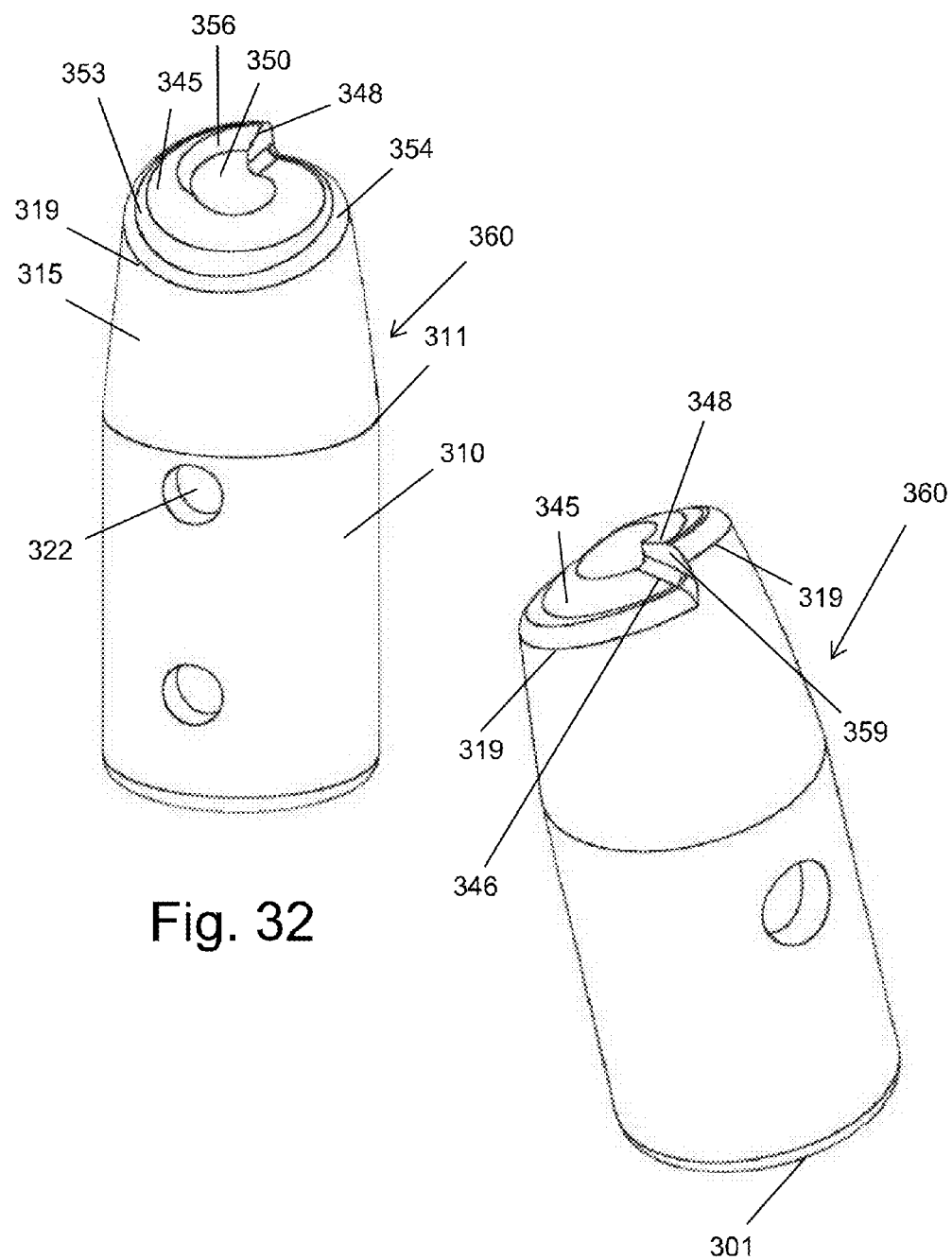
FIGS. 32 and 33 are two perspective views of the drill unit of FIG. 31, respectively, each taken at opposite sides thereof.

Reference is now made to FIGS. 32 and 33, which illustrate two perspective views of drill unit 360, each taken at opposite sides thereof. Drill unit 360 has an outer annular wall comprising a proximal portion 310 of a uniform diameter on the order of 1 mm, e.g. an outer diameter of 1.16 mm and an inner diameter of 0.94 mm, and a tapered distal portion 315 whose diameter gradually decreases from the interface 311 with proximal portion 310 to its distal edge 319. A plurality of access holes 322 substantially perpendicular to the longitudinal axis of drill unit 360 are formed in proximal portion 310. Access holes 322 serve as openings through which the hollow shaft is able to be welded to the drill unit, for example by laser welding.

Drill unit 360, which may be made of stainless steel, has a spiraled end face 345, the distance to which from straight proximal edge 301 of drill unit 360 gradually increases, from a first end face edge 346 to a maximum value at second end face edge 348 constituting the single cutting edge. A surface 359, which may be configured by a substantially planar distal portion that may be substantially perpendicular to proximal edge 301 and by a concave proximal portion, defines the discontinuity between first edge 346 and second edge 348 and the resulting tooth height, which may range from 0.1-0.4 mm, e.g. 0.2 mm.

End face 345 has a central bore 350 for accommodating passage therethrough of the guidewire. A rounded transitional surface 356, which borders cutting edge 348 and a portion of end face 345, extends radially inwardly to bore 350 and is specially formed to define an oblique cutting edge disposition ranging from 15-25 degrees, e.g. 20 degrees, with respect to a plane perpendicular to proximal edge 301. Peripheral rounded edges 353 and 354 surrounding end face 345 circumferentially and spatially extend to the distal edge 319 of distal portion 315, to ensure that all surfaces of drill unit 360, with the exception of cutting edge 348, are rounded and atraumatic to a blood vessel when the atherectomy device is advanced over the guidewire.

Figure 34:
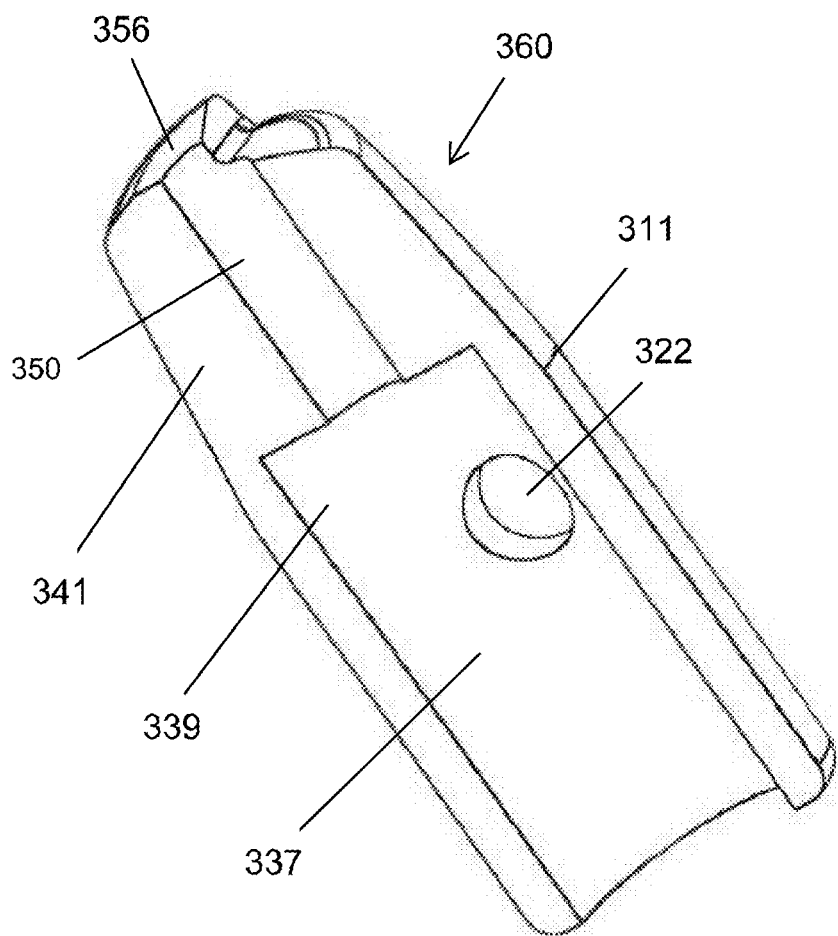
FIG. 34 is a longitudinal cross sectional view of the drill unit of FIG. 32.

As shown in the longitudinal cross sectional view of FIG. 34, a cylindrical recess is formed within the interior face 341 of drill unit 360, to define a cavity 337 having a cavity wall 339 for retaining the hollow shaft. Cavity 337 is formed from proximal edge 301 to a portion slightly proximally to interface 311.

Figure 35:
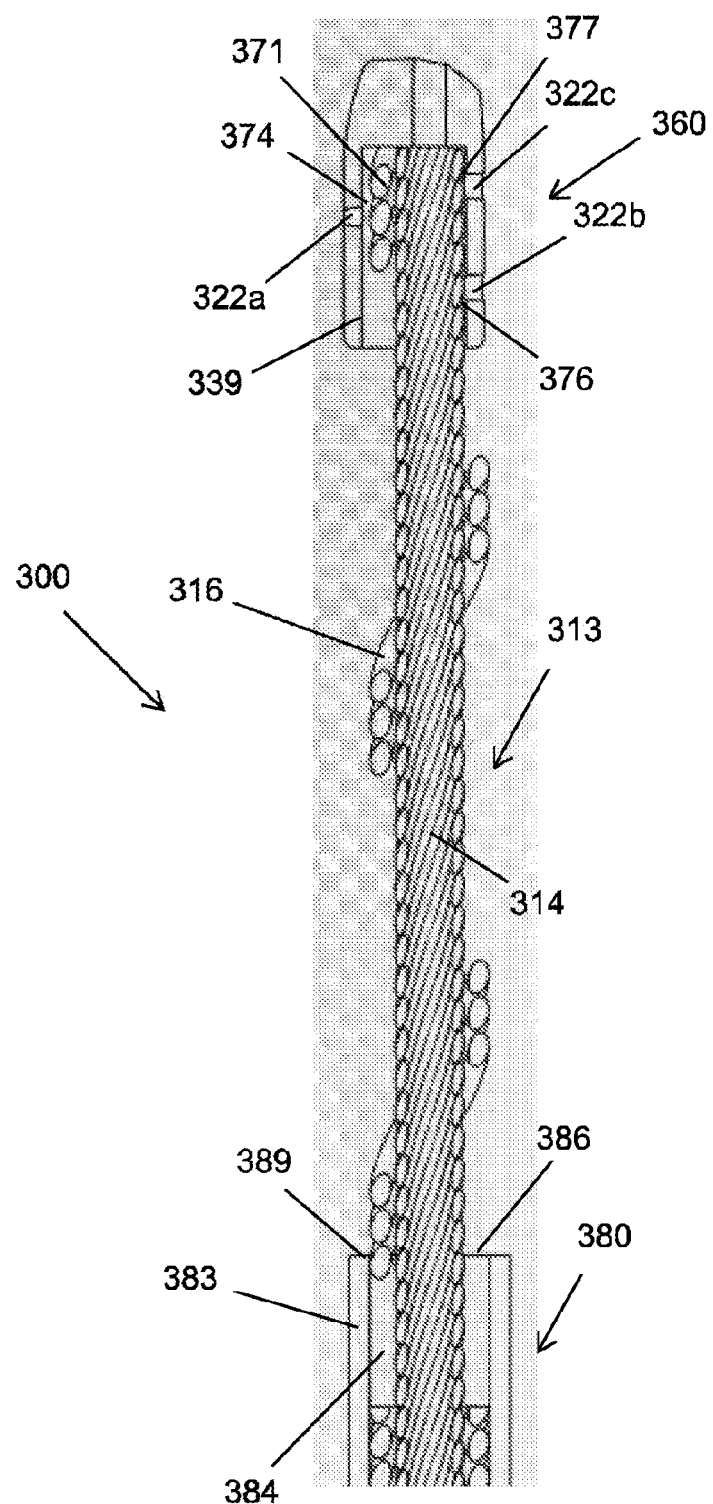
FIG. 35 is a longitudinal cross sectional view of FIG. 31.

FIG. 35 illustrates a longitudinal cross sectional view of FIG. 31. Hollow shaft 313 is shown to comprise tubular inner portion 314 and outer portion 316 in the form of a set of wires, e.g. three wires, which is wound about tubular inner portion 314. Prior to connection with drill unit 360, the distal end of inner portion 316 is connected to outer portion 314 of the hollow shaft at weld point 371. After the distal end of hollow shaft 313 is positioned within cavity 337 (FIG. 34), inner portion 316 is connected to cavity wall 339 at weld point 374 via access hole 322a and outer portion 314 is connected to cavity wall 339 at weld points 376 and 377 via access holes 322b and 322c, respectively.

Stress relief unit 380 is in the form of a hollow tube 383, with which inner portion 314 is in movable engagement. While inner portion 314 extends to the motor for rotatably driving the hollow shaft, outer portion 316 is considerably shorter and extends only to the distal end 386 of stress relief unit 380. The proximal end of outer portion 316 is connected to inner face 389 of tube 383 by weld point 389.

When inner portion 314 is proximally displaced by means of the adjusting member, its distal end approaches its proximal end, allowing the inner portion to expand in order to remove atheromatous material upon operation of the motor. By virtue of the angular disposition of outer portion 316 with respect to the longitudinal axis of inner portion 314, the inner portion is configured to expand eccentrically. If so desired, the inner portion may be configured to expand concentrically. Considerable stress is relieved during a material removal operation by having the ends of the inner portion welded distant from the point of material removal.

The distance to which the inner portion is proximally displaced may be limited by means of a spacer fitted on the inner portion, for example in abutment with distal end 386 of stress relief unit 380.

Atherectomy device 300 allows for more efficient removal of atheromatous material by being provided with drill unit 360. For more common types of blood vessel occlusions characterized by accumulation of atheromatous material on only the walls of the blood vessel while the remaining blood vessel remains unobstructed, rotation of drill unit 360 accompanying rotation of hollow shaft 313 does not effect any material removal.

Following observation of a chronic total occlusion (CTO), for example by radiopaque observation, within a blood vessel, or of an occlusion to a lesser degree, operation of the motor, for example at a speed of 5000 rpm or more, will cause the drill unit to rotate and the cutting edge to remove atheromatous material from the blood vessel lumen. Repeated proximal and distal movement of the rotating drill unit will also contribute to the disintegration of the hard atheromatous material that has accumulated during conditions of a CTO. The drill unit may be operated when the cutting unit is not expanded.

It will be appreciated that one or both of the drill unit and the stress relief unit may be employed in any other embodiment described herein.

Figure 36:
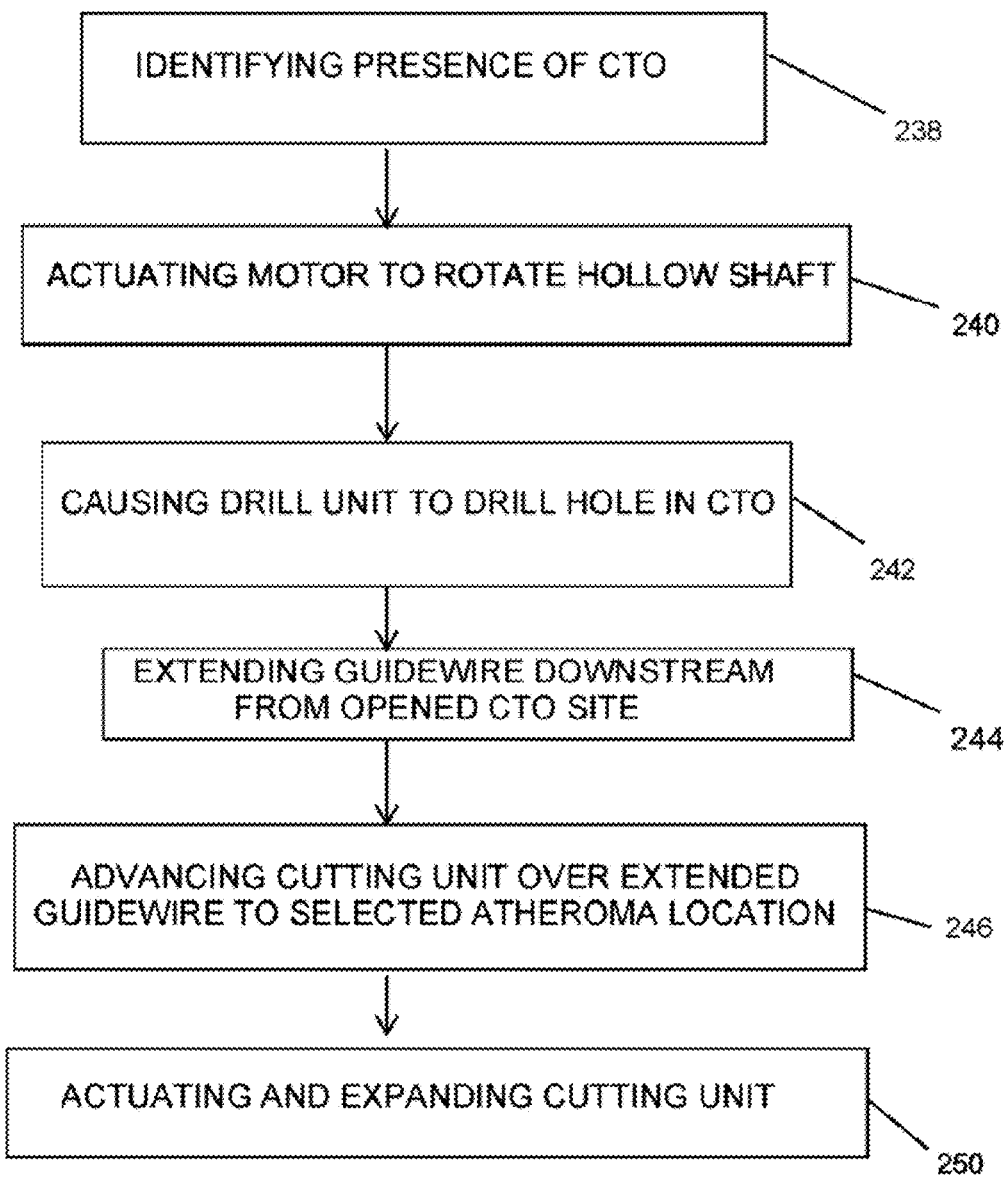
FIG. 36 is a method for drilling a hole in a total occlusion, according to one embodiment of the invention.

With reference now to FIG. 36, a drilling operation is performed after identifying the presence of a CTO in step 238. While the guidewire is extended to, but upstream from, the CTO, the motor for rotating the hollow shaft is activated in step 240. Since the drill unit is connected to the hollow shaft, the drill unit is caused to rotate and to drill a hole in step 242 within the CTO which is sufficiently large to permit passage therethrough of the guidewire and then of the collapsed cutting unit. After the guidewire is extended downstream from the opened CTO site in step 244, the cutting unit is advanced over the extended guidewire to a selected atheroma location in step 246, whereupon the cutting unit is expanded in step 250. The other steps are the same as in FIG. 30.

FIGS. 23-27 illustrate another embodiment wherein the hollow shaft is produced by micro-laser cutting of a tube, so that it will be afforded good flexibility with excellent torque transmission characteristics. In this embodiment, the cutting unit is also produced by micro-laser cutting, and is formed integrally with the outer tubular portion.

Figure 23:
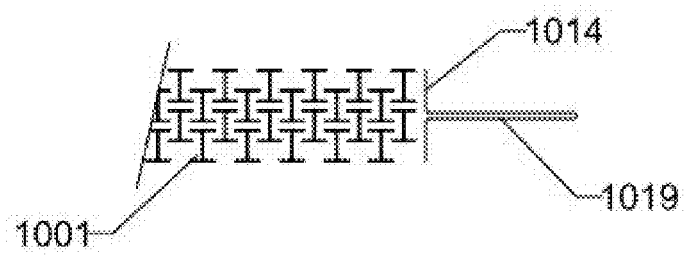
FIG. 23 is an illustration of a pattern formed by a micro-laser cutting technique.
Figure 25:
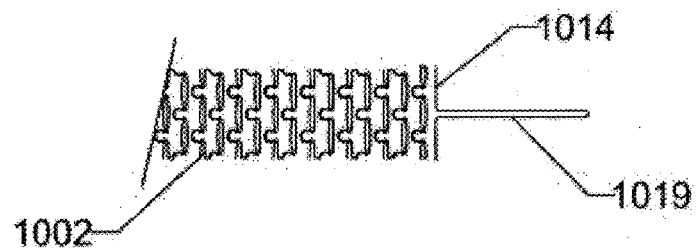
FIG. 25 is an illustration of a pattern formed by a micro-laser cutting technique.
Figure 27:
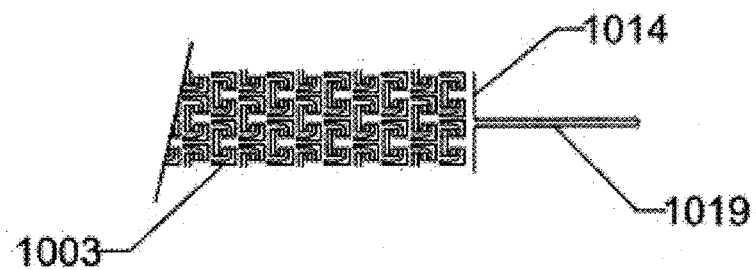
FIG. 27 is an illustration of another pattern formed by a micro-laser cutting technique.

Three exemplary cutting patterns 1001, 1002 and 1003 are shown in FIGS. 23, 25 and 27, respectively, while the flexible cutting unit 1019 is integrally formed with the outer tubular portion 1014. The inner tube portion may also be produced with similar patterns. Expansion of cutting unit 1019 is made possible by attaching its distal end to the inner tube portion, or to a holder connected to the inner tube portion.

Figure 24:
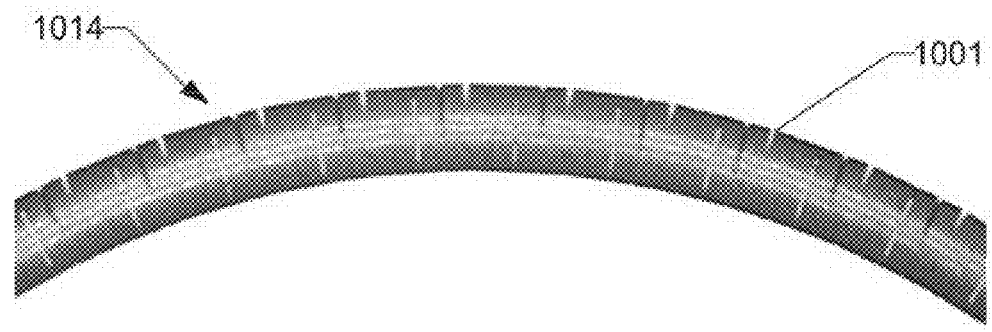
FIG. 24 is a picture of an outer tubular portion produced from the pattern of FIG. 23.
Figure 26:
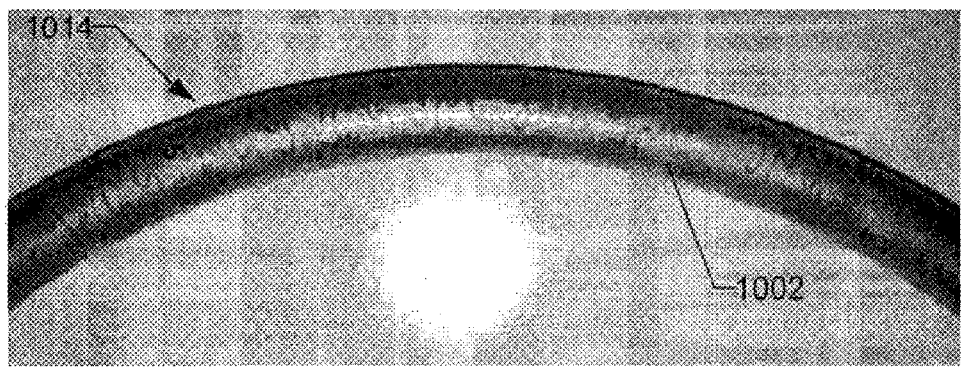
FIG. 26 is a picture of an outer tubular portion produced from the pattern of FIG. 23.

FIGS. 24 and 26 are pictures of two outer tubular portions 1014 produced with patterns 1001 and 1002, respectively.

The flexible outer and inner tubular portions of the hollow shaft may also be produced by cutting a spiral cut along the wall of a tube according to conventional laser cutting techniques.

Reference is now made to FIGS. 16-19, which illustrate the operation of guidewire introduction unit 150 adapted to cooperate with adjusting member 9. The hollow shaft has been removed, for clarity.

Guidewire introduction unit 150 comprises a seal compression initiator 110 and a split seal 111, e.g. made of rubber, which is compressible by initiator 110. Compression initiator 110 has an annular inner planar guidewire contactable wall 113, an outer wall 114 contactable with a proximal, longitudinally extending flange 124 of adjusting member 9, and a cross element 116 extending between walls 113 and 114.

Adjusting member 9 has a main body 137 that is receivable in catheter body 8 (FIG. 4) and of a similar shape, e.g. rectilinear in longitudinal cross section. A central passageway 139 through which guidewire 10 and the hollow shaft are introducible is formed in adjusting member 9. Passageway 139 is formed with a conical section 109 that is more narrowed near proximal surface 143 of the adjusting member, for guiding the guidewire tip into introduction unit 150. Seal 135 for engaging the hollow shaft and the inner face of the catheter body is attached to the distal face of adjusting member 9.

A recess for accommodating the displacement of wall 114 is formed at the proximal outer surface of adjusting member 9, defining flange 124, which extends significantly beyond planar proximal surface 143. A seal section 111 is attached to the corresponding inner face portion of flange 124.

Figure 16:
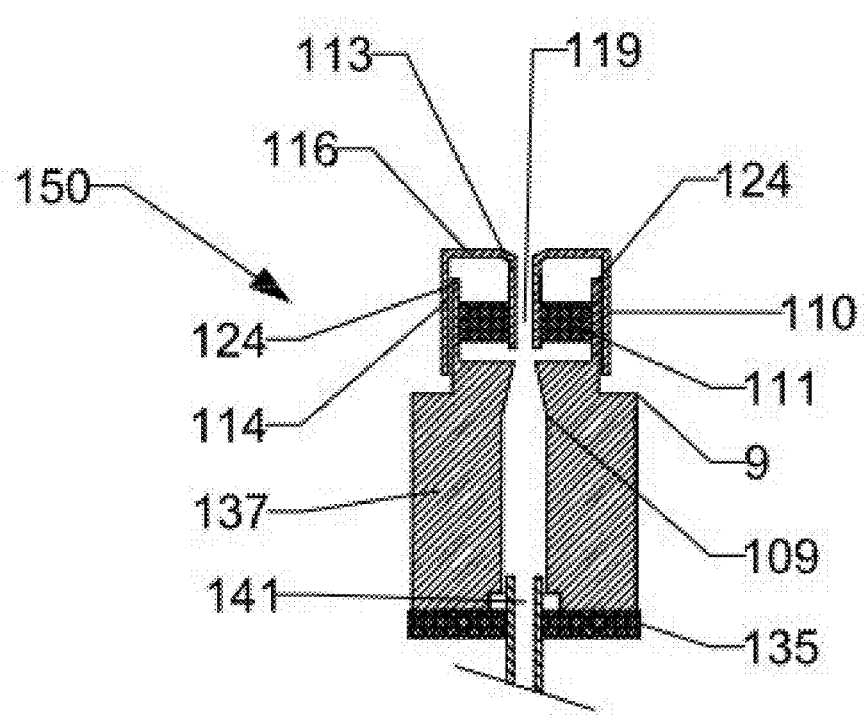
FIG. 16 is a longitudinal cross section of a guidewire introduction unit, shown in an open position.

FIG. 16 illustrates a cross section of introduction unit 150 in an "OPEN" position, whereby inner wall 113 thereof is in abutting relation with seal 111 to cause the latter to become laterally compressed, forming an opening 119 that adjoins central passageway 139. A compressing force is applied, during distal displacement of the seal compression initiator 110 when inner wall 114 slides along flange 124, by inner wall 113 onto seal 111 in the vicinity of the interface of the seal sections, to produce the central opening 119.

Figure 17:
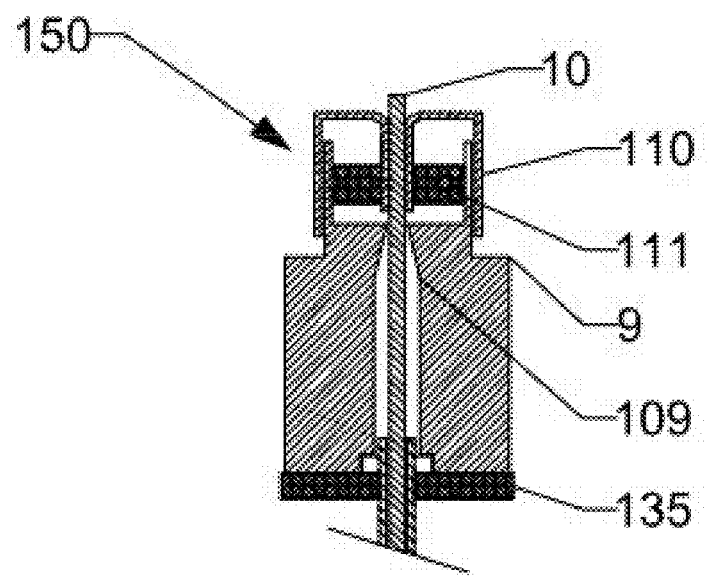
FIG. 17 is a longitudinal cross section of the guidewire introduction unit of FIG. 16, shown in a starting position.

In FIG. 17, introduction unit 150 is shown in a "STARTING" position, after guidewire 10 has been introduced within central opening 119 and is in abutment with inner wall 113.

Figure 18:
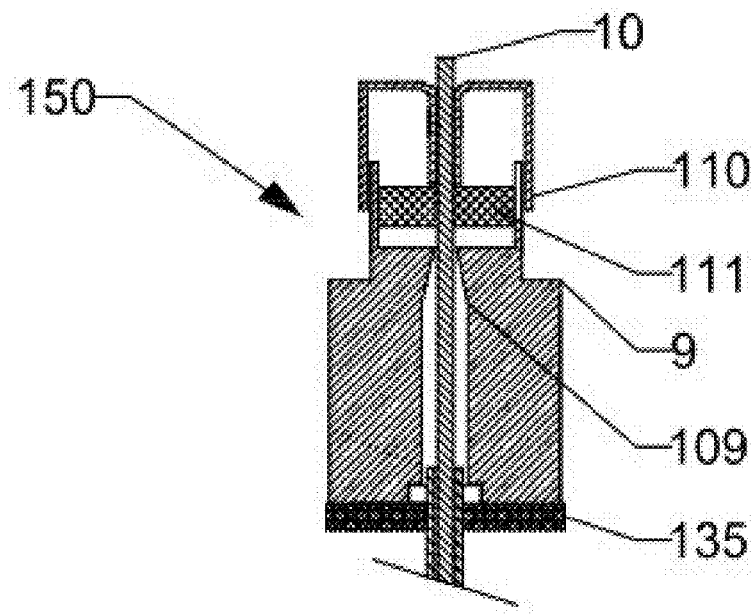
FIG. 18 is a longitudinal cross section of the guidewire introduction unit of FIG. 16, shown in a working position.

In FIG. 18, introduction unit 150 is shown in a "WORKING" position whereby initiator 110 is proximally displaced with respect to adjusting member 9 and separated from seal sections 111. The seal sections 111 are therefore caused to be in sealing engagement with guidewire 10, to prevent ingress of air and liquids from one side of seal 111 to the other while the guidewire is passing through. While introduction unit 150 is in the "WORKING" position, adjusting member 9 is able to be longitudinally displaced with respect to the catheter body.

Figure 19:
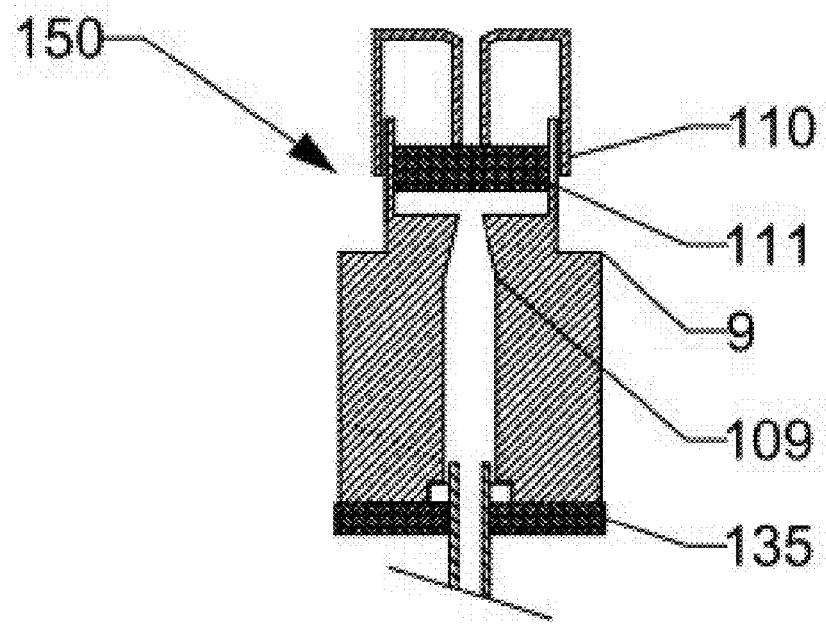
FIG. 19 is a longitudinal cross section of the guidewire introduction unit of FIG. 16, shown in a closed position.

When the guidewire is removed from the atherectomy device and introduction unit 150 is in a "CLOSED" position, as shown in FIG. 19, the seal sections 111 are in contact with each other to prevent ingress of air and liquids from one side of the seal to the other.

While some embodiments of the invention have been described by way of illustration, it will be apparent that the invention can be carried out with many modifications, variations and adaptations, and with the use of numerous equivalents or alternative solutions that are within the scope of persons skilled in the art, without exceeding the scope of the claims.

The invention claimed is:

1. An expandable atherectomy device, comprising:
a) a flexible catheter tube;
b) a guidewire along which said catheter tube is advanceable and which is insertable into a blood vessel until its distal end is adjacent to a site of atheromatous material, said guidewire being introducible through said catheter tube;
c) a rotatably motor-driven flexible hollow shaft that is slidable over said guidewire and is coaxial with a longitudinal axis of said guidewire, wherein said hollow shaft comprises directly radially interconnected and torque transmitting, inner and outer tubular portions that are simultaneously rotatable in response to operation of a motor while one of said inner and outer tubular portions slides with respect to the other in a direction substantially parallel to said longitudinal axis;
d) a flexible and eccentrically expandable cutting unit having two longitudinally separated ends, wherein said cutting unit, when eccentrically expanded, is eccentrically rotatable about said longitudinal axis to facilitate disintegration and removal of atheromous material from said blood vessel, and wherein one of said two longitudinally separated ends is connected to a distal end of said hollow shaft; and
e) an actuator which is operable to induce selective expansion of said cutting unit in response to an actuated action which causes said two longitudinally separated ends of said cutting unit to be brought closer together and to flex to achieve an expanded diameter.

2. The device according to claim 1, wherein the cutting unit—
has a straight configuration substantially parallel to the longitudinal axis when set to a collapsed condition and an arcuate bowed configuration when set to an expanded condition; or
is formed integrally with the outer tubular portion; or
has a plurality of elongated elements which are wound about, and positioned obliquely with respect to, the longitudinal axis in such a way that, when expanded, only one diametrical end of the shaft is surrounded by said elongated elements for a given axial length of the shaft; or
is made of a shape-memory alloy which, when heated, will change its shape and be set to a bowed configuration when expanded.

3. The device according to claim 2, further comprising an elastic skirt surrounding the cutting unit for ensuring non-traumatic contact with blood vessel walls.

4. The device according to claim 2, wherein the outer tubular portion is—
configured by the plurality of elongated elements wound about the longitudinal axis such that more than one of said plurality of elongated elements are longer than the other elongated elements that do not distally extend beyond the outer tubular portion, said more than one longer elongated elements functioning as the cutting unit when distal ends thereof are connected to a distal end of the inner tubular portion; or
configured by a proximal relatively rigid portion and a distal relatively flexible portion, wherein said proximal relatively rigid portion is connected to said distal relatively flexible portion by discontinuously applied laser welding.

5. The device according to claim 4, wherein two or more adjacent elongated elements of the plurality of elongated elements are connected together.

6. The device according to claim 1, further comprising two longitudinally spaced cutting unit holders that are carried by the hollow shaft at the distal end thereof, wherein the inner tubular portion is distally longer than the outer tubular portion, and one of said two holders is connected to a distal region of the inner tubular portion, and one of said two holders is connected to a distal region of the outer tubular portion.

7. The device according to claim 1, further comprising a housing body in which the motor for rotatably driving the hollow shaft is housed, and a connection means for connecting the catheter tube to a distal tip of said housing body, wherein the motor is drivingly engaged with the outer tubular portion.

8. The device according to claim 7, further comprising an aspiration system for removal of disintegrated atheroma particles which is in communication with the interior of the catheter tube, said aspiration system comprising a vacuum pump, a first aspiration line extending from an annular space between the housing body distal tip and the outer tubular portion to said vacuum pump, a collection bag to which are drawn the disintegrated atheroma particles, and a second aspiration line extending from said vacuum pump to said collection bag.

9. The device according to claim 7, wherein the connection means is a telescopingly expandable adaptor.

10. The device according to claim 7, wherein the motor is also drivingly engaged with an element configured to generate a vacuum for inducing aspiration of disintegrated atheroma particles.

11. The device according to claim 7, wherein the actuator is a longitudinally displaceable adjusting member, to a distal face of which is connected a seal which is sealingly engaged with the housing body and with the inner tubular portion, proximal displacement of said adjusting member causing the inner tubular portion to be displaced in a similar direction, whereby to set the cutting unit to a bowed configuration.

12. The device according to claim 11, wherein the adjusting member is formed with a cavity in which is seated a rotating bearing connected to the inner tubular tube portion.

13. The device according to claim 11, wherein the outer tubular portion is formed with a window having a proximal and distal edge, one of said proximal edge and distal edge being contactable by a pin attached to the inner tubular portion at a corresponding extreme position of the adjusting member, whereby to limit the longitudinal displacement of the adjusting member and to radially interconnect the inner and outer tubular portions.

14. The device according to claim 1, further comprising a drill unit connected to, and distally protruding from the distal end of the hollow shaft, for drilling a chronic total occlusion present in the lumen of the blood vessel, said drill unit configured with—
   a) an outer annular wall comprising a proximal portion of a uniform diameter which is configured with a cavity wall to which an outer portion of the hollow shaft constituting the eccentrically rotatable and expandable cutting unit is connected, and with a tapered distal portion whose diameter gradually decreases from an interface with said proximal portion to a distal edge of said distal portion;
   b) a spiraled end face having first and second edges, said second edge constituting a single cutting edge and being discontinuous with respect to said first edge, wherein a distance to said spiraled end face from a straight proximal edge of said proximal portion gradually increases from said first edge to a maximum value at said second edge; and
   c) a bore provided centrally with said spiraled end face for accommodating the guidewire; and
   d) peripheral rounded edges surrounding said spiraled end face that circumferentially and spatially extend to the distal edge of said distal portion to ensure that all surfaces of said drill unit, with the exception of the cutting edge, are rounded and atraumatic to the blood vessel.

15. The device according to claim 1, further comprising a pin attached to the inner tubular portion and a window formed with the outer tubular portion which has a width only slightly more than said pin, wherein the inner and outer tubular portions are radially interconnected while rotating simultaneously by means of said pin and by means of a widthwise edge of said window.

16. A method for removing atheroma, comprising the steps of:
   a) providing the expandable atherectomy device of claim 1;
   b) actuating said cutting unit to initiate temporary and elastic expansion of said cutting unit; and
   c) causing disintegration and removal of atheromatous material from blood vessel walls during asymmetric rotation of said cutting unit about said longitudinal axis relative to said hollow shaft.

17. The method according to claim 16, wherein the cutting unit is selectively and gradually actuated until its diameter approximates the diameter of the blood vessel at the site of the atheroma, to maximize atheromatous material removal; or the atherectomy device is advanced over the guidewire inserted within the blood vessel while the cutting unit is in a collapsed condition until a distal end of the device protrudes from the catheter tube and is adjacent to the atheroma.

18. The method according to claim 16, wherein the removed material is aspirated through a lumen of the catheter tube.

19. The method according to claim 16, wherein the catheter tube is replaced in order to access a different sized blood vessel.

20. The method according to claim 16, further comprising the step of drilling an occlusion present in the lumen of a blood vessel by a drill unit connected to the cutting unit.

* * * * *